United States Patent
Goldberg et al.

(10) Patent No.: US 10,398,655 B2
(45) Date of Patent: *Sep. 3, 2019

(54) TWO-STAGE MICROPARTICLE-BASED THERAPEUTIC DELIVERY SYSTEM AND METHOD

(71) Applicant: Privo Technologies, Inc., Peabody, MA (US)

(72) Inventors: Manijeh Nazari Goldberg, Newburyport, MA (US); Aaron Manzi, Peabody, MA (US); Brandon LaPorte, Peabody, MA (US); Amritpreet Birdi, Peabody, MA (US)

(73) Assignee: Privo Technologies, Inc., Peabody, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/436,651

(22) Filed: Feb. 17, 2017

(65) Prior Publication Data
US 2017/0239189 A1    Aug. 24, 2017

Related U.S. Application Data

(60) Provisional application No. 62/296,599, filed on Feb. 18, 2016, provisional application No. 62/336,209, (Continued)

(51) Int. Cl.
*A61K 9/50* (2006.01)
*A61K 31/7068* (2006.01)
(Continued)

(52) U.S. Cl.
CPC ........ *A61K 9/5036* (2013.01); *A61K 9/0053* (2013.01); *A61K 9/485* (2013.01);
(Continued)

(58) Field of Classification Search
CPC .. A61K 31/282; A61K 9/0053; A61K 9/5161; A61K 9/205
See application file for complete search history.

(56) References Cited

U.S. PATENT DOCUMENTS

| 4,895,724 A | 1/1990 | Cardinal et al. ............. 424/418 |
| 2003/0017195 A1 | 1/2003 | Mitragotri et al. ........... 424/449 |

(Continued)

FOREIGN PATENT DOCUMENTS

| AU | 2014218717 B2 | 8/2014 | ............ A61K 9/51 |
| DE | 10313427 A1 * | 1/2004 | ......... C08B 37/003 |

(Continued)

OTHER PUBLICATIONS

Luangtana-anan et al., Pharmaceutical Development and Technology, 10: 189-196 (Year: 2005).*

(Continued)

*Primary Examiner* — Kortney L. Klinkel
(74) *Attorney, Agent, or Firm* — Sunstein Kann Murphy & Timbers LLP

(57) ABSTRACT

A system for delivery of a therapeutic agent to a site in mucosal tissue is provided. The system includes a porous, mucoadhesive polymeric matrix having a first and a second opposed surfaces. The matrix is formed by a composition including chitosan, a hydration promoter, a microparticle adhesion inhibitor, and a microparticle aggregation inhibitor. A plurality of microparticles are embedded within the matrix. The microparticles contain a therapeutic agent and have a coating around the therapeutic agent. The first surface of the matrix is configured to be attached to the site in the mucosal tissue and the matrix is configured to provide controlled release of the microparticles through the first (Continued)

surface. The coating of the microparticles includes chitosan so as to provide controlled release of the agent from the microparticles.

10 Claims, 32 Drawing Sheets

(56) References Cited

OTHER PUBLICATIONS

Koh, PK, et al., "A Systematic Review of the Function and Complications of Colonic Pouches," *Int J Colorectal Dis.*, vol. 22, pp. 543-548 (2007).

Kulkarnia, A.R., et al., "In-Vitro Release Kinetics of Cefadroxil-Loaded Sodium Alginate Interpenetrating Network Beads," *European Journal of Pharmaceutics and Biopharmaceutics*, vol. 51, No. 2, pp. 127-133, Mar. 2001.

Lai, S., et al., "Mucus-Penetrating Nanoparticles for Drug and Gene Delivery to Mucosal Tissues," *Adv Drug Deliv Rev.*, vol. 61, No. 2, pp. 158-171, Feb. 27, 2009.

Laksitorini, M., et al., "Pathways and Progress in Improving Drug Delivery Through the Intestinal Mucosa and Blood-Brain Barriers," *Ther. Deliv.*, vol. 5, No. 10, pp. 1143-1163, Oct. 2014.

Liu, Z., et al., "Polysaccharides-Based Nanoparticles as Drug Delivery Systems," *Adv. Drug Deliv. Rev.*, vol. 60, No. 15, pp. 1650-1662, Dec. 2008.

Macrae, Finlay A., M.D., et al., "Clinical Presentation, Diagnosis, and Staging of Colorectal Cancer," *UpToDate*, 20 pages, Retrieved from the Internet on Mar. 8, 2017: http://www.uptodate.com/contents/clinical-presentation-diagnosis-and-staging-of-colorectal-cancer.

MD Consult, "Anatomy and Histology of the Small and Large Intestine," 18 pages, Retrieved from the Internet on Mar. 8, 2017: http://jpck.zju.edu.cn/jcyxjp/files/ge/05/MT/0511.pdf.

Misono, S., et al., "Incidence of Suicide in Persons With Cancer," *Journal of Clinical Oncology*, vol. 26, No. 29, pp. 4731-4738, Oct. 10, 2008, Retrieved from the Internet on Mar. 9, 2017: http://jco.ascopubs.org/content/26/29/4731.full.

Murata, Y., et al., "Use of Floating Alginate Gel Beads for Stomach-Specific Drug Delivery," *Eur J Pharm Biopharm.*, vol. 50, Issue 2, pp. 221-226, Sep. 2000.

Nagpal, K, et al., "Chitosan Nanoparticles: A Promising System in Novel Drug Delivery," *Chemical and Pharmaceutical Bulletin*, vol. 58, No. 11, pp. 1423-1430, Nov. 2010.

National Cancer Institute, Fact Sheet, Surveillance, Epidemiology, and End Result Program (SEER)—Cancer of the Anus, Anal Canal, and Anorectum, 9 pages, Retrieved from the Internet on Mar. 7, 2017: https://seer.cancer.gov/statfacts/html/anus.html.

National Cancer Institute, Fact Sheet, Surveillance, Epidemiology, and End Result program (SEER)—Cancer of the Colon and Rectum, 9 pages, Retrieved from the Internet on Mar. 15, 2017: https://seer.cancer.gov/statfacts/html/colorect.html.

National Psoriasis Foundation, "Psoriasis Foundation," 4 pages, Retrieved from the Internet on Apr. 6, 2017: https://www.psoriasis.org/.

National Psoriasis Foundation, "Causes and Triggers," 6 pages; Retrieved from the Internet on Apr. 6, 2017: https://www.psoriasis.org/about-psoriasis/causes.

Original Author: Dr. Colin Trudy Current Version: Dr. Roger Henderson, "Prescribing for Children," *Patient Platform Limited*, 3 pages, Last Checked: Jan. 26, 2015—Retrieved from the Internet on Mar. 7, 2017: http://patient.info/doctor/prescribing-for-children.

Patil, P., et al., "A Review on Ionotropic Gelation Method: Novel Approach for Controlled Gastroretentive Gelispheres," *Int J Pharm Pharm Sci.* vol. 4, Suppl. 4, pp. 27-32 (2012).

Paun, B.C., et al., "Postoperative Complications Following Surgery for Rectal Cancer," *Annals of Surgery*, vol. 251, No. 5, pp. 807-818 (2010).

Ryan, David, P., MD, et al., "Clinical Features, Staging, and Treatment of Anal Cancer," 10 pages, Retrieved from the Internet on Mar. 8, 2017: http://www.uptodate.com/contents/clinical-features-staging-and-treatment-of-anal-cancer.

Shaw, D., et al., "The Intestinal Mucosal Atrophy and Adaptation," *World Journal of Gastroenterology*, vol. 18, Issue 44, pp. 6357-6375, Nov. 28, 2012.

The HPV and Anal Cancer Foundation, Living with Anal Cancer—Causes & Risk Factors—8 pages, Retrieved from the Internet on Mar. 7, 2017: http://www.analcancerfoundation.org/living-with-anal-cancer/anal-cancer-risk-factors-causes/.

The HPV and Anal Cancer Foundation, "Living With Anal Cancer/Treatment for Anal Cancer," 18 pages, Retrieved from the Internet on Mar. 8, 2017: http://www.analcancerfoundation.org/living-with-anal-cancer/anal-cancer-treatment/.

The Oral Cancer Foundation, "Information—Support—Advocacy Research . . . and Hope," n.d. Web. Jan. 21, 2016; 3 pages. Retrieved from the Internet on Mar. 9, 2017: http://oralcancerfoundation.org/.

The Oral Cancer Foundation, "Mucositis," n.d. Web. Jan. 21, 2016, 14 pages Retrieved from the Internet on Mar. 9, 2017: http://oralcancerfoundation.org/complications/mucositis/.

Saramento, B., et al., "Chitosan-Based Systems for Biopharmaceuticals: Delivery, Targeting and Polymer Therapeutics," *John Wiley & Son, Ltd.*, 564 pages, Mar. 2012.

Weinberg, M.A., et al., "Assessing Oral Malignancies," *American Family Physician*, vol. 65, No. 7, pp. 1379-1384, Apr. 1, 2002.

Written by Kann, A., et al., "Burns: Types, Treatments, and More," *Healthline* Newsletter,15 pages, Retrieved from the Internet on Apr. 5, 2017: http://www.healthline.com/health/burns?m=0#Overview1.

Willett, Christopher G., MD, et al., "Adjuvant Therapy for Resected Rectal Adenocarcinoma," 5 pages Retrieved from the Internet on Mar. 8, 2017: http://www.uptodate.com/contents/adjuvant-therapy-for-resected-rectal-adenocarcinoma.

Youssef, N.N., et al., "Management of Intractable Constipation With Antegrade Enemas in Neurologically Intact Children," *Journal of Pediatric Gastroenterology & Nutrition*, vol. 34, No. 4, pp. 402-405, Apr. 2002.

Zhang, H., et al., "Monodisperse Chitosan Nanoparticles for Mucosal Drug Delivery," *Biomacromolecules*, vol. 5, No. 6, pp. 2461-2468 (2004).

Zhang, Z, et al., "Polymeric Nanoparticles-Based Topical Delivery Systems for the Treatment of Dermatological Diseases," *Nanomedicine and Nanobiotechnology*, vol. 5, Issue 3, pp. 205-218, May/Jun. 2013.

Vázquez, Lantes, M. Authorized Officer, Written Opinion of the International Searching Authority, PCT/US2017/018514, 9 pages, dated Jul. 6, 2017.

CocoaBio Tech, "Preparation and Use of a Dry Ice/Ethanol Bath," 2 pages, Cited from Internet: www.koko.gov.my/CocoaBioTech/General%20Lab4.html; Aug. 29, 2018.

LarkinWeb, "Lab Freezing Bath Temperatures," 3 pages, Cited from Internet: https://larkinweb.co.uk/science/freezing_bath_temperatures.html; Aug. 29, 2018.

Lee, B., et al., "Controlled-Release of Tetracycline and Lovastatin by Poly(D,L-Lactide-co-Glycolide Acid)-Chitosan Nanoparticles Enhances Periodontal Regeneration in Dogs," *International Journal of Nanomedicine*, pp. 285-297, Jan. 18, 2016.

Mohandas, A., et al., "Drug Loaded Bi-Layered Sponge for Wound Management in Hyperfibrinolytic Conditions," *Journal of Materials Chemistry B*, Issue 20, vol. 3, pp. 5795-5805, Jun. 2015.

Sigma-Aldrich, Hanks' Balanced Salts [HBSS], 1 page, Retrieved from Internet: https://www.sigmaaldrich.com/content/dam/sigma-aldrich/docs/.../1/h1387pis.pdf; Apr. 2007.

\* cited by examiner

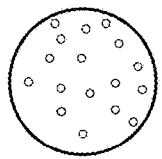
FIGURE 22A
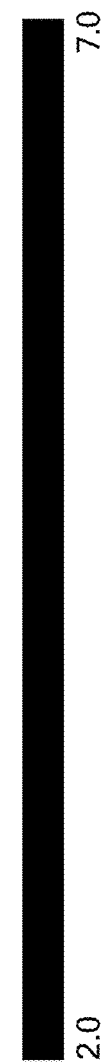
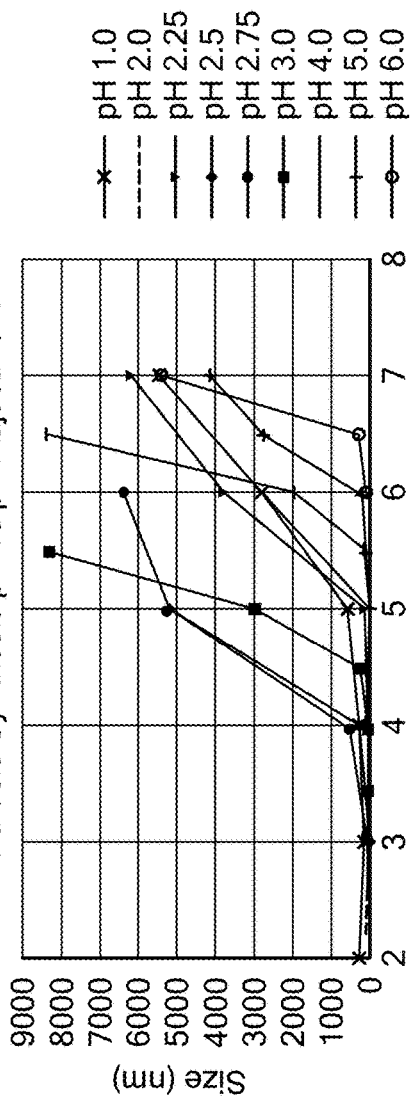
FIGURE 22B
FIGURE 22C

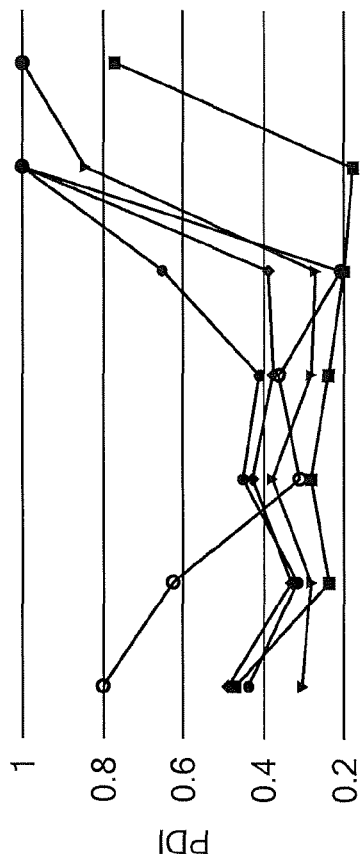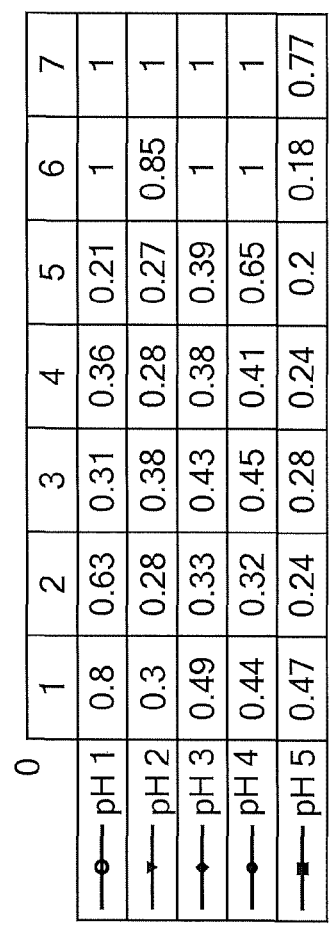
FIGURE 23C

FIGURE 26A

| synthesized at pH=3.4 | | | | | |
|---|---|---|---|---|---|
| pH=1 | pH=2 | | pH=4 | pH=5 | pH=6 |
| PDI=0.49 | PDI=0.33 | | PDI=0.38 | PDI=0.39 | PDI=1 |
| Size=229.2 | Size=82.71 | | Size=77.18 | Size=59.43 | Size=3583 |

FIGURE 26B

| synthesized at pH=1 | | | | | |
|---|---|---|---|---|---|
| pH=2 | pH=3 | | pH=4 | pH=5 | pH=6 |
| PDI=0.63 | PDI=0.31 | | PDI=0.36 | PDI=0.21 | PDI=1 |
| Size=359.1 | Size=67.24 | | Size=79.21 | Size=101.9 | Size=3447 |

FIGURE 26C

| synthesized at pH=2 | | | | | |
|---|---|---|---|---|---|
| pH=3 | pH=4 | | pH=5 | pH=6 | pH=7 |
| PDI=0.38 | PDI=0.28 | | PDI=0.27 | PDI=0.85 | PDI=1 |
| Size=49.91 | Size=117.3 | | Size=71.99 | Size=3783 | Size=2984 |

FIGURE 26D

| synthesized at pH=4 | | | | | |
|---|---|---|---|---|---|
| pH=1 | pH=2 | pH=3 | pH=4 | pH=5 | pH=6 |
| PDI=0.44 | PDI=0.32 | PDI=0.45 | PDI=0.41 | PDI=0.65 | PDI=1 |
| Size=118.4 | Size=99.71 | Size=1783 | Size=195.7 | Size=297.9 | Size=2384 |

FIGURE 26E

| synthesized at pH=5 | | | | | |
|---|---|---|---|---|---|
| pH=1 | pH=2 | pH=3 | pH=4 | pH=6 | pH=7 |
| PDI=0.47 | PDI=0.24 | PDI=0.38 | PDI=0.24 | PDI=0.18 | PDI=0.77 |
| Size=216 | Size=116.2 | Size=111.8 | Size=71.66 | Size=110.2 | Size=4270 |

TWO-STAGE MICROPARTICLE-BASED THERAPEUTIC DELIVERY SYSTEM AND METHOD

CROSS REFERENCE TO RELATED APPLICATIONS

The present application claims the benefit of these U.S. provisional applications: Ser. No. 62/336,405, filed on May 13, 2016; Ser. No. 62/296,599, filed on Feb. 18, 2016; and Ser. No. 62/336,209, filed on May 13, 2016. Each one of these applications is hereby incorporated herein by reference in its entirety.

STATEMENT REGARDING FEDERALLY SPONSORED RESEARCH

This invention was made with government support under grants nos. R44CA192875-01 and number R44DE023725-03 awarded by The National Institutes of Health. The government has certain rights in the invention.

TECHNICAL FIELD

The present invention relates to systems for delivery of a therapeutic agent to a mucosal tissue, and in particular to systems with a porous polymeric matrix including chitosan and a plurality of microparticles embedded within the matrix.

BACKGROUND

Cancers affecting the mucosae of the body are a growing public health concern. Oral cancer alone affects over 640,000 people annually worldwide and over 40,000 in the US. The incidence is on the rise due to an increased affliction with oral HPV, which is cancer causing. Treatment methods include surgery and systemic chemotherapy administered intravenously, often in combination. Surgery is often ineffective due to the difficulty associated with identifying margins surrounding oral tumors. This inability to completely remove tumors during surgery contributes to oral cancer's high rate of recurrence. Systemic chemotherapy is often used but lacks targeting and exposes the patient's entire body to damaging chemotherapeutics. This method can be dose limiting due to exposure within the blood stream and other organs, as precautions must be taken in consideration of the safety of this systemic exposure. Systemic delivery often results in damaging side effects from toxic drugs reacting with the body. These include neurotoxicity, nephrotoxicity, kidney failure, hair loss, nausea and mucositis.

In addition, oral cancer is among the most debilitating diseases emotionally as well as physically. Permanent disfiguration can occur after surgical resection of oral tumors. The patient's ability to eat, drink, or properly speak after surgery can also become impaired or not possible. In part for these reasons, oral cancer is considered the most expensive cancer to treat. The costs associated with surgery and chemotherapy themselves are substantially high. However, in the case of oral cancer there also are significant costs required to reconstruct the face, neck or other regions affected by the large removal of tissue. These can include jawbone or oral tissue reconstruction. Further, these procedures can also leave the patient hospitalized in recovery for long periods of time, which also contributes to substantial rehabilitative costs post-operation. These costs can add up to a sum that has been recognized as the highest costs associated with cancer, and can exceed the amount of US$150,000.

In addition to monetary cost and other physical side effects, emotional side effects also speak to the especially tragic and debilitating effect of oral cancer compared to other cancers and diseases. The emotional toll on oral cancer patients can be far greater than that of other diseases, primarily due to the physical deformity (including physical appearance and lack of clear speech) that results from treatment. The potential loss of significant portions of the tongue can be what leads to permanently impaired speech and even taste. The severity of this emotional effect can be fully understood when the suicide rates associated with other diseases are compared. The suicide rate of patients suffering from oral cancer is among the highest as compared to other cancers, and is about three times the rate of several other types of cancer. These consequences of traditional treatment methods for oral cancer illustrate why an alternative treatment method is desperately needed to address this unmet need and patient suffering.

Anal cancer accounts for 2.5 percentage of all digestive system malignances in the US, and approximately 8,000 new cases are diagnosed annually. The incidence of anal cancer in the general population has increased over the last 3 decades. Additionally, colorectal cancer (CRC) is a common and lethal disease. It is estimated that approximately 134,490 new cases of large bowel cancer are diagnosed annually in the US, including approximately 95,270 colon and 39,220 rectal cancers. This cancer remains the third most common cause of cancer death in the United States. Approximately 49,190 Americans are expected to die of large bowel cancer each year.

One of the differences between colorectal cancer and anal cancer are the risk factors that can cause each. Primary risk factors for colorectal cancer include age, genetics, race, diabetes, obesity, lack of exercise and smoking. In contrast, the primary cause of anal cancer has been the increase in prevalence of human papillomavirus (HPV).

As it pertains to anal cancer, almost all cases of anal cancer are caused by HPV, which is cancer causing, the presence of the HPV genome has been identified in 80%-85% of the cases of anal cancer. The HPV is able to live only in squamous epithelial cells that are found on the surface of the skin and on moist surfaces—mucosal surfaces. The virus is transmitted through skin contact. Sexual activity and other skin contact has been a primary driver of anal cancer. The primary driver of the rise in incidence is due to the rise of HPV. Smoking is another risk factor for anal cancer as it spreads carcinogens throughout the entire body and also reduces the immune system's ability to fight the HPV virus. Over 90% of anal cancer is squamous cell carcinoma, with the other 10% including more rare forms of cancer including basal cell carcinoma, adenocarcinoma, and malignant melanomas.

1. Anal Cancer Treatment:

Contrary to current perception, anal cancer is a very significant and debilitating disease. Treatment can include surgery, radiation, chemotherapy, and combinations thereof, often resulting in significant side effects. Despite the various choices, these treatment options remain ineffective in many cases at eliminating tumors and preventing death. As stated in the background, the percentage of patients surviving 5 years after treatment ranges between 45-85% according to the stage of the disease. The relatively low survival rate is unimpressive considering that anal cancer is typically discovered at early stages. According to US government statistics, 49% of anal cancer is localized at the time of diagnosis. An additional 31% exists regionally in the area; fewer than 20% are node-positive, while only 13% is discovered metastasized. The low 5 year survival rate despite these localized statistics suggests that current treatment options are not optimal and may be considered ineffective at treating anal cancer.

1.1 Surgery: While surgical treatment for anal cancer as the standard of care has since been replaced by chemotherapy, it is still used as a means of tumor reduction when chemotherapy shows little effect. This radical procedure can require the removal of the anus, rectum, and sigmoid colon, with creation of a permanent colostomy. An ostomy as it pertains to anal and rectal cancer is a surgically created opening in the abdominal wall that is used to divert bodily waste during and after anal surgery. For anal cancer, the most common ostomy is the colostomy. Instead of expulsion via the anus, feces and other waste pass through the opening of this and into an external collection bag. A specialized nurse is required to teach procedures regarding caring and washing of the ostomy and surrounding area. The process of surgically creating and personally maintaining the ostomy and collection bag can be very painful, emotionally challenging, can result in infection, and can be very expensive.

Developments of new strategies were directed at preservation of the anal sphincter. Surgery has been associated with local failure in up to half of cases, and five-year survival rates are approximately 50%-70%. In the past, surgical treatment with abdominoperineal resection (APR) (APR) was routinely performed for anal cancer. The radical procedure required removal of the ano-rectum with creation of a permanent colostomy. The overall probability of five-year survival was 40-70%, with a perioperative mortality of 3%. When surgery is used, side effects are extensive and debilitating. The most common immediate complication (in 32% of patients) is intra-abdominal or pelvic abscess, other complications include nerve injury (the autonomic nerves that affect both sexual and urinary function may be injured), postoperative sexual or urinary dysfunction (10-60%), urologic injury, perineal wound, and complications related to the ostomy. Current treatment approaches reserve surgical therapy for patients with recurrent or persistent disease after chemoradiotherapy. Although prognosis is poor overall, an APR offers the potential for long-term survival. Local excision is performed by several surgeons for small, local perianal cancer, where sphincter function will not be compromised by adequate surgical resection.

As mentioned before, in more serious (refractory or recurrent) cases of anal cancer, APR is performed, in these cases, a permanent colostomy is needed, and permanent damaging side effects are common. Failure to control anal cancer and complications of treatment are alternative indications for a colostomy, but in most cases, colostomy is required for recurrent tumor.

1.2 Chemotherapy: Systemic chemotherapy is often used but lacks targeting and exposes the patient's entire body to damaging chemotherapeutics. This method can be dose limiting due to exposure within the blood stream and other organs, as precautions must be taken in consideration of the safety of this systemic exposure. Systemic delivery often results in damaging side effects from toxic drugs reacting with the body. These include neurotoxicity, nephrotoxicity, kidney failure, hair loss, nausea and mucositis. As an alternative to surgery, chemotherapy in addition to radiation are also used as methods to treat anal tumors. The current standard of care uses initial concurrent combination of chemotherapy and radiation for patients with anal canal squamous cell carcinoma, even with small, local tumors. When chemotherapy is used, temporary central venous catheters or peripherally inserted central catheters may be used on an individual. Side effects from treatment include those typical to systemic chemotherapy. These include nausea, hair loss, kidney damage, low blood cell count, mouth sores and a compromised immune system. Since chemotherapy is currently delivered systemically throughout the body, there are dose limiting factors which can result in lower dosages being administered than what is considered optimal.

1.3 Radiation: Forms of radiation administered include external radiation or brachytherapy (internal radiotherapy, aiming to spare the surrounding normal structures). These can be used as a treatment method in combination with chemotherapy, and are very extensive. They are commonly administered 5 days a week for 5 to 6 weeks. In addition to the side effects, this high frequency of administration contributes to the strenuous nature of this treatment method. Side effects can persist post-treatment and include irritation, pain during bowel movements and urination, vaginal pain or vaginal stenosis (for women) and erectile dysfunction or impotence (for men). Sexual and gastrointestinal dysfunction can occur and will often last throughout the remainder of the patients' life. The incidence of late toxicity from radiation such as anal ulcers, stenosis, and necrosis, is also dose-dependent.

2. Rectal Cancer Treatment:

2.1. Surgery: Different surgical options are available, according to the stage, location, differentiation of the tumor. Superficially invasive, small rectal cancers managed with limited surgical procedure-trans-anal excision (TAE). Disadvantages of TAE alone are the high recurrence rate (up to 31%), potential compromise for cure, and the need for additional wider resection when positive to cancer margins are found. Since the majority of patients have more deeply invasive tumors, more extensive surgery is required, surgical options include total mesorectal excision (TME), low anterior resection (LAR) that includes rectum and sigmoid colon removal.

These surgical options carry a variety of complications including risk of perioperative mortality. Wound infections, fecal frequency or urgency, the need for rectal reconstruction with its complications, anastomosis leak that leads to considerably high rates of morbidity and possible mortality. Patients also risk functional derangements or, even, incontinence. Sexual and bladder function may also be adversely affected, probably because of injury to autonomic nerves.

The last surgical option is the abdominoperineal resection (APR) with its potential complications (mentioned above).

2.2 Radiotherapy: radiotherapy combined with chemotherapy can be used as a neoadjuvant (induction chemoradiotherapy) can be used for locally advanced or node-positive tumors, adjuvant treatment aims to improve local control and survival, and reduce recurrence.

2.3 Chemotherapy: As mentioned before, chemotherapy is used in combination with radiation as part of neoadjuvant or adjuvant treatment. The regimen of chemotherapy used is typically FOLFOX (5-FU, leucovorin, and oxaliplatin) or CapeOx (capecitabine and oxaliplatin). These chemotherapies are given systemically leading to systemic toxicities as mentioned prior.

Anal and rectal cancer together account for a very significant portion of cancer cases within the United States and worldwide, however due in part to the side effects and limited efficacy described above, still lack an ideal safe and effective treatment option. In order to address this severe unmet need, provided herein is an alternative, more effective treatment option for colorectal and anal diseases. Agents commonly delivered in large doses systemically to treat these conditions have been reformulated for localized delivery and retention, resulting in higher local concentration of agents while a lower overall dosage has been administered. The present invention aims to overcome the shortcomings, side effects, and lack of efficacy of current treatment options.

Difficulties in delivering therapeutic agents to mucosal tissues can also be a hurdle to the treatment of diseases affecting the gastrointestinal (GI) tract. For example, over three million people are diagnosed with *C. difficile* colitis each year in the United States alone, and such disease can be caused by antibiotics which destroy the body's natural bacteria. GI diseases, including inflammation, IBD and its variants can also stem from malnutrition, unsanitary living conditions, exposure to bacteria, and other causes. These causes explain a significantly higher prevalence in developing nations, particularly those in Africa and Southeast Asia. Children under five years of age are particularly vulnerable to these conditions. There exists substantial risk of life-threatening complications such as dehydration, sepsis, kidney failure, colon perforation, and death. These are diseases of a very debilitating, painful and widespread nature and represent a chronically underserved market.

Despite the drawbacks of traditional drug administration routes, they remain effective in certain cases at releasing therapeutic, diagnostic and/or prophylactic agents into the gastrointestinal tract. However, when employing these routes, local delivery of agents not only within the intestine but also through the intestinal mucosa remains very difficult. The mucosa layer on the intestinal wall presents a formidable barrier to adhesion and absorption of such agents, such as biologics, peptides, pharmaceuticals and nutraceuticals which are commonly delivered in standalone forms. Few compositions can penetrate this viscous, slippery material to reach the tissue and cells beneath.

Pertaining to targeted delivery, it is difficult for most substances to become attracted to these cells long enough to deliver an effective amount of the therapeutic, diagnostic and/or prophylactic agent. This remains one of the principal difficulties limiting the efficacy of treatments delivered to the GI tract. Likewise, sufficient targeting to regions within the GI tract remains highly difficult due to the complex makeup of the GI tract. Highly acidic levels within the stomach and varying pH levels within different sectors of the intestine contribute to targeting difficulty, particularly to particle-based therapies. For example, the pH of the duodenum of a fasted patient can be approximately 4.5 while the jejunum exhibits a pH closer to 6.5. A delivery system would in this example have to be able to withstand the stomach pH (1.5-2.5) in addition to the pH of the duodenum in order to be delivered into the jejunum. This scenario is present across the GI tract depending on the region and fed vs. fasted condition of the patient.

SUMMARY OF THE EMBODIMENTS

In accordance with a first set of representative embodiments of the invention, a system for delivery of a therapeutic agent to a site in mucosal tissue is provided. The system includes a porous, mucoadhesive polymeric matrix having first and second opposed surfaces. The matrix is formed by a composition including chitosan, a hydration promoter, a microparticle adhesion inhibitor, and a microparticle aggregation inhibitor. A plurality of microparticles are embedded within the matrix. The microparticles contain a therapeutic agent and have a coating around the therapeutic agent. The first surface of the matrix is configured to be attached to the site in the mucosal tissue and the matrix is configured to provide controlled release of the microparticles through the first surface. The coating of the microparticles includes chitosan so as to provide controlled release of the agent from the microparticles. Optionally, the hydration promoter is selected from the group consisting of ethylene glycol, propylene glycol, beta-propylene glycol, glycerol and combinations thereof. Also optionally, the microparticle adhesion inhibitor is a non-ionic polymer, and, as a further option, the non-ionic polymer is HPMC. Additionally, as an option, the microparticle aggregation inhibitor is selected from the group consisting of monosaccharides, disaccharides, sugar alcohols, chlorinated monosaccharides, chlorinated disaccharides, and combinations thereof. Also optionally, the microparticles further include sodium tripolyphosphate. Optionally, in the system there is a free quantity of the therapeutic agent, embedded directly in the matrix, and not otherwise coated with chitosan, wherein the free quantity of the therapeutic agent constitutes between 20-80% of a total quantity of therapeutic agent in the system. Optionally, the second surface is permeable to water. As a further option, the second surface includes a material selected from the group consisting of a polyacrylate adhesive, a non-woven polyester fabric, or combinations thereof. Optionally, the chitosan in the matrix and the chitosan in the microparticles is pure chitosan. As a further option, the average diameter of the microparticles is from about 500 nm to about 2000 nm.

In another embodiment, there is provided a porous, mucoadhesive polymeric matrix formed by a composition including chitosan, a hydration promoter, a microparticle adhesion inhibitor, and a microparticle aggregation inhibitor. In accordance with yet another set of representative embodiments of the invention, there is provided a method for manufacturing a therapeutic agent delivery system. The method includes forming a first mixture with a plurality of microparticles. The microparticles contain a therapeutic agent and have a coating around the therapeutic agent, the coating including chitosan. The method also includes forming a second mixture from ingredients including the first mixture, chitosan, a hydration promoter, a microparticle adhesion inhibitor, and a microparticle aggregation inhibitor. The method further includes freezing the second mixture in a bath containing an aqueous alcoholic solution at a temperature above the freezing temperature of the aqueous alcoholic solution and at most −40° C., to form a frozen layer precursor. Finally the method includes drying the frozen layer precursor, to form a porous polymeric matrix with microparticles embedded within the matrix. Optionally, the bath further contains dry ice. Also optionally, the alcohol of the aqueous alcoholic solution is ethanol. As a further option, the aqueous alcoholic solution is from about 90 wt % ethanol to about 99 wt % ethanol. Optionally, the method further includes applying a second layer precursor to the frozen layer precursor, to form a solid comprising a first layer and a second layer. Optionally, the second layer comprises a therapeutic agent. Also optionally, the wherein the drying is under vacuum.

BRIEF DESCRIPTION OF THE DRAWINGS

The foregoing features of embodiments will be more readily understood by reference to the following detailed description, taken with reference to the accompanying drawings, in which:

FIG. 5A shows fluorescent FITC and Cy5 above the tissue shortly after application of the device according to one of the embodiments of the present invention.

FIG. 5B shows FITC beginning to permeate the tissue after 30 minutes. FIG. 5C shows the green FITC permeating deeper into the tissue after 1 hour.

FIG. 18C: Fluorescence intensity was 23% higher after 60 min incubation vs. after 30 min due to higher NP uptake.

FIG. 22A is a schematic drawing of a particle according to an embodiment of the present invention. FIG. 22B includes a list of parameters which may be modified to control the degradation of particles according to embodiments of the present application.

FIG. 22C illustrates release of encapsulated agents from particles as the pH increases.

FIG. 23C: pH change to polydispersity index (PDI). The PDI is a key factor of NPs stability. A PDI of 1 signifies that the solution is incredibly polydisperse, indicating that particles have fallen apart.

FIGS. 24A and 24B illustrate the sensitivity of LPs synthesized from chitosan chloride rather than the raw chitosan polymer. LPs made from chitosan chloride proved to be more fragile and sensitive to pH changes than the raw counterpart. FIGS. 24C and 24D illustrate the level of modulation and control that can be held over LP properties from chitosans of different compositions and molecular weights using sodium nitrite.

In FIGS. 25A and 25B is plotted the effect of different pre-processing time in relation to NP charge and size respectively. In FIGS. 25C and 25D are graphed the effects of using different concentrations of a preprocessing agent such as sodium nitrite.

FIGS. 26A-26E: Tables showing the polydispersity (PDI) and average size in nanometers of particles synthesized at various pH levels which have been designed to remain stable at desired secondary pH levels.

DETAILED DESCRIPTION OF SPECIFIC EMBODIMENTS

Figure 1:
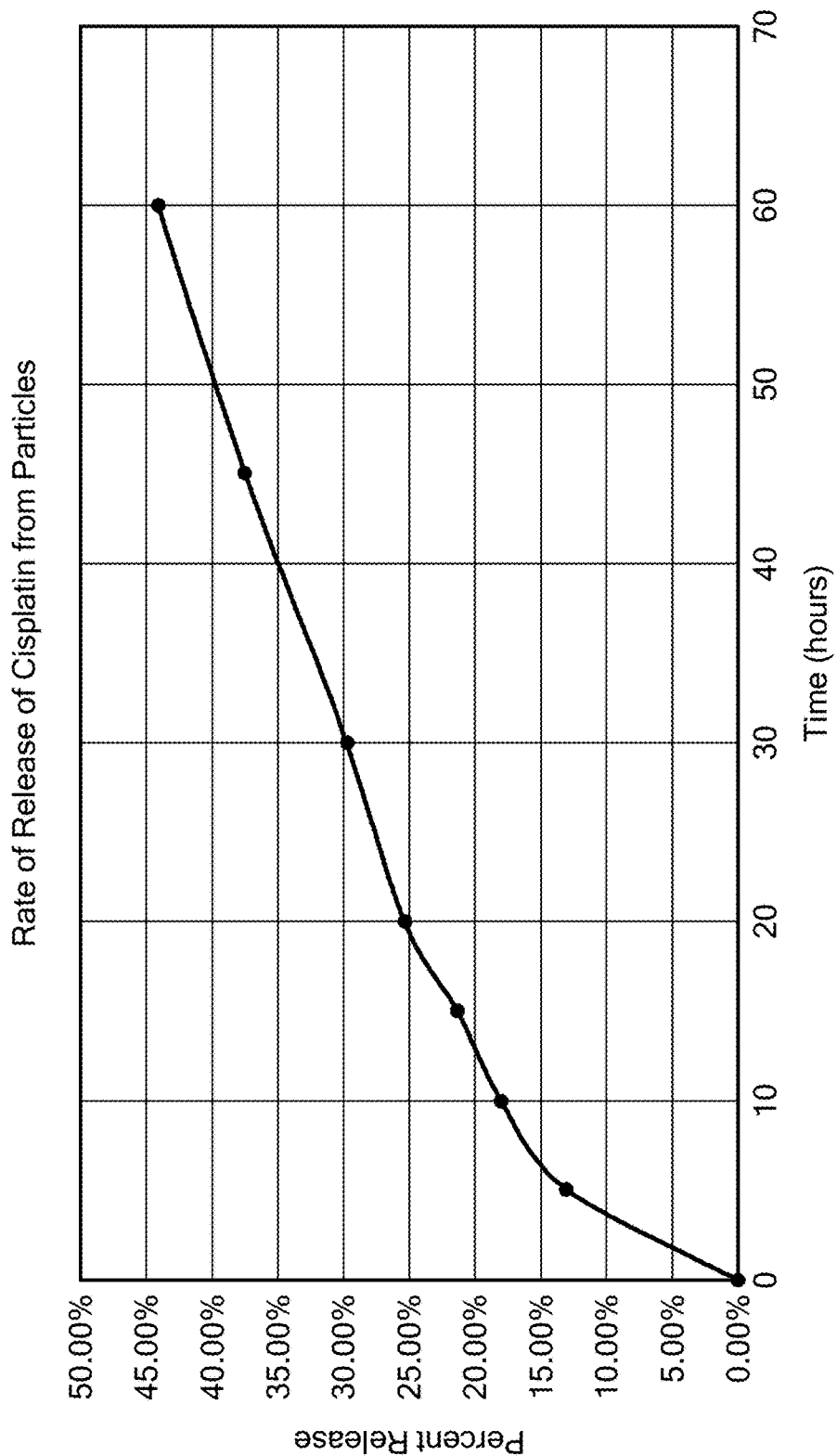
FIG. 1 is a graph showing the release profile of example particles which may be included within a multi-layered device according to embodiments of the present invention.

Definitions. As used in this description and the accompanying claims, the following terms shall have the meanings indicated, unless the context otherwise requires:

A "polymer" is a molecule having at least 100 units of a monomer.

"Microparticles" are sets of particles having an average diameter of at least 200 nm to at most 2000 nm.

"Nanoparticles" are sets of particles having an average diameter of at least 1 nm to below 200 nm.

A "particle diameter" or "particle size" is the length of the longest straight axis between two points on the surface of the particle.

A "pure chitosan" is a chitosan that is not a salt of chitosan.

A "microparticle adhesion inhibitor" is an additive that lowers the attractive forces between a polymeric matrix and particles embedded therein. As a result, the particles can move through the matrix at a faster rate than in the absence of the adhesion inhibitor.

A "microparticle aggregation inhibitor" is an additive that lowers the tendency of particles embedded in a matrix to aggregate when the matrix is subjected to freezing. As a result, the particles are less likely to suffer from damage or destruction when the freezing takes place.

A "mucoadhesive" material is characterized as having the ability to adhere to mucosal membranes in the human body.

A matrix is "porous" when a fraction of its volume is void space. In some instances, the void space is accessible from the outer surface of the matrix, so that items present in the void space, such as microparticles, may migrate to and from the outer surface.

"Mucosal tissue" is tissue having an associated mucosa. In particular, mucosal tissue includes the mucosa and also tissue underlying the mucosa. A "site in mucosal tissue", where, for example, a cancerous tumor is present may involve not only the mucosa but also tissue underlying the mucosa.

"Polydispersity index" (PDI) or simply, "dispersity" is a measure of the heterogeneity of sizes of a set of particles, for example microparticles in a mixture.

"Zeta potential" (ZP) is a measure of the overall charge that a particle acquires in a particular medium. The ZP may be measured on a Zetasizer Nano instrument.

"Permeation" is the ability to pass through or penetrate, a mucosa, its underlying tissue, or both.

"Biocompatible" refers to the ability of a biomaterial to perform its desired function with respect to a medical therapy, without eliciting any significant undesirable local or systemic effects in the recipient or beneficiary of that therapy, but generating the most appropriate beneficial cellular or tissue response in that specific situation, and optimizing the clinically relevant performance of that therapy.

"HPMC" refers to hydroxypropyl methylcellulose, also known as hypromellose.

"Biodegradable" refers to a property of the materials that is capable of being broken down especially into innocuous products by the action of living things.

"Kilo count per second" (Kcps)", mean count rate (in kilo counts per second (kcps)). For example, the threshold may be set such that when the count rate of the sample is lower than 100, the measurement should be aborted, meaning the concentration of the sample is too low for measurements. A sample with suitable Kcps can be considered a stable sample with idea concentration for measurement.

"Mesh" refers to a device, sponge, wafer, or like product which contains elements incorporated within it to be released from the mesh when it is applied to a mucosa.

A "system for delivery of a therapeutic agent based on a polymeric matrix and microparticles" may also be referred to as an "agent delivery device" or as a "delivery patch".

Unless otherwise specified, the term "wt %" refers to the amount of a component of a system for delivery of a therapeutic agent, as expressed in percentage by weight.

Unless otherwise specified, the "molar mass" of a polymer is intended to mean the number average molar mass of the polymer molecules.

Improved Matrix and Particle Device

In a first aspect, the present application provides improvements to the technology described in published U.S. application number US 2014/0234212, entitled "Targeted Buccal Delivery of Agents", which is hereby incorporated herein by reference in its entirety.

In a first set of representative embodiments, there are provided systems for delivery of a therapeutic agent based on a polymeric matrix and microparticles which are improved by the addition of a hydration promoter to the matrix. Example hydration promoters include hygroscopic compounds such as glycols, for instance ethylene glycol, propylene glycol, beta-propylene glycol, and glycerol. Exemplary concentration ranges for the amount of hydration promoter include from about 0.001 to about 10 wt %, from about 0.01 to about 5 wt %, and from about 0.1 to about 1 wt %.

Without wishing to be bound to any particular theory, it is believed that the hydration promoter increases moisture absorption by the delivery system. This increase in hydration enables the rapid release and permeation of the microparticles from the matrix. It is also believed that the hydration promoter improves uniformity and durability by acting as a cryoprotectant during the manufacturing process of the delivery system. Again without being bound to any particular theory, it is believed that the hydration promoter acts as a "spacer" between ice crystals and matrix polymer molecules, to ensure a uniform freezing pattern. The resulting structure is more flexible, uniform, and durable than in the absence of the hydration promoter.

Figure 34:
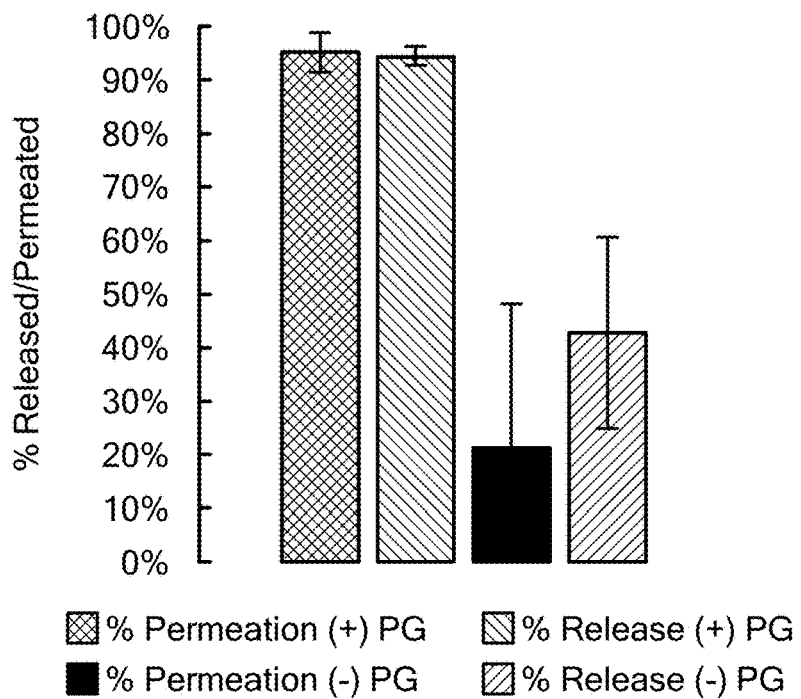
FIG. 34 is a chart comparing permeation and release of chitosan particles from a patch having a chitosan matrix in the presence (+PG) or absence (−PG) of propylene glycol according to embodiments of the present invention.

To illustrate the improvement in performance imparted by hydration promoters, patches including a chitosan polymer matrix and chitosan microparticles were manufactured with and without propylene glycol (PG) in the matrix. The particle release and permeation of the patches was measured for both types of patch, and the experiment was run in triplicate. As reported in the chart of FIG. 34, the average percentage of permeation in the presence of propylene glycol ((+)PG) was 94% with a standard deviation of about 3%, which dropped to 43% with a standard deviation of 27% in the absence of propylene glycol ((−)PG). The percentage of release in the presence of propylene glycol was 95% with a standard deviation of about 3%, as against 21% with a standard deviation of 41% without PG. Clearly, patches with PG performed markedly better than those without, and release and permeation numbers were more reproducible as shown by the smaller standard deviations.

In another set of representative embodiments, there are provided delivery devices improved by the addition of an adhesion inhibitor. Without wishing to be bound to any particular theory, it is believed that when the matrix and particles are made of materials bearing polar or ionically charged moieties, such as chitosan, the mobility of the particles suffers. In the instance of chitosan, it is believed that the interactions between acetyl and amine moieties of the polymer cause the particles to adhere to the matrix and inhibit their release.

It has been found that the inclusion of an adhesion inhibitor can mitigate adhesion of the matrix with the particles. Without being bound to any particular theory, it is believed that the adhesion inhibitor acts as a "spacer" between the chitosan of the particles and the chitosan in the body of the matrix, releasing the particles and allowing for improved drug release profiles. Representative example adhesion inhibitors include non-ionic polymers such as hydroxypropyl methylcellulose (HPMC). Depending on the application, the molar mass of the non-ionic polymer may be from about 1 kDa to about 200,000 kDa, while its viscosity may vary from about 10 cps to 100,000 cps. In representative embodiments, the molar mass of the non-ionic polymer is from about 10 kDa to 30 kDa, and its viscosity from about 10 cps to about 100 cps. Depending on the application, the amount of adhesion inhibitor may be from about 0.1 wt % to about 99 wt %. In some embodiments, the amount of adhesion inhibitor is from about 0.1 wt % to about 25 wt %.

In a further set of representative embodiments, delivery devices improved by the addition of an aggregation inhibitor are disclosed. Processes for manufacturing the delivery devices include freezing steps during which ice crystals may form within the matrix. Such crystals can force the microparticles into each other, creating particle aggregates where the particles are damaged or destroyed. Again without wishing to be bound to any particular theory, it is believed that aggregation inhibitors exert a cryoprotectant action by forming crystal microstructures which prevent aggregation of the particles. Carbohydrates and carbohydrate derivatives provide exemplary types of aggregation inhibitors, including monosaccharides, disaccharides, sugar alcohols, chlorinated monosaccharides, and chlorinated disaccharides such as sucralose. Depending on the application, the amount of aggregation inhibitor in the patch may be in the range from about 0.1 to about 50 wt %. In some embodiments, the amount of aggregation inhibitor is from about 1 to about 10 wt %.

In another set of representative embodiments, improved pure chitosan microparticles are provided. Traditional chitosan particles are manufactured with salts of chitosan characterized by a high degree of deacetylation and bearing electrically charged moieties, for example chitosan chloride and chitosan glutamate. It has been found that better results are provided if the particles are made from pure chitosan, a material characterized by not being a salt, that is, with its amine groups unprotonated, and having a degree of deacetylation of at least 70%. In particular, the particles are characterized by larger diameters than traditional particles. In some embodiments, the average diameter of the pure chitosan particles may range from about 200 to about 2000 nanometers. In other embodiments, the average diameter ranges from about 500 to about 2000 nanometers, and in additional embodiments from 500 to 1000 nm.

In a further improvement, chitosan microparticles improved by the addition of sodium tripolyphosphate (STPP) are provided. Without wishing to be bound to any particular theory, it is believed that the STPP functions as a cross-linker to form the particles by acting as a negative counter-ion to the positively charged amine groups on chitosan. This electrostatic interaction forms ionic bonds that support the structure of the particles. Also without wishing to be bound to any particular theory, it is believed that the presence of sodium as positive counterion renders STPP a more effective crosslinker than other TPP salts.

It has also been found that when the matrix includes a free quantity of the therapeutic agent, embedded directly in the matrix and not otherwise coated with chitosan in the particles, the device is therapeutically more effective than comparable matrices which include either only a free quantity of the therapeutic agent or only therapeutic agent coated with chitosan. In representative embodiments, the free quantity of the therapeutic agent constitutes between 20-80% of the total quantity of therapeutic agent in the delivery system.

FIG. 1 is a graph showing the release profile of example particles having an average diameter in the range of 500 to 2000 nm. The graph shows the rate of release of the encapsulated agent from the nanoparticles over 60 hours. Cisplatin was used for this experiment due to its use in the treatment of oral cancer and its ease of detection via atomic absorption spectrometry (AAS). Cisplatin is platinum-based, and AAS can detect amounts of platinum as small as 5 µg/L. The graph shows 45% of cisplatin released from NPs over 60 hours.

Figure 35A:
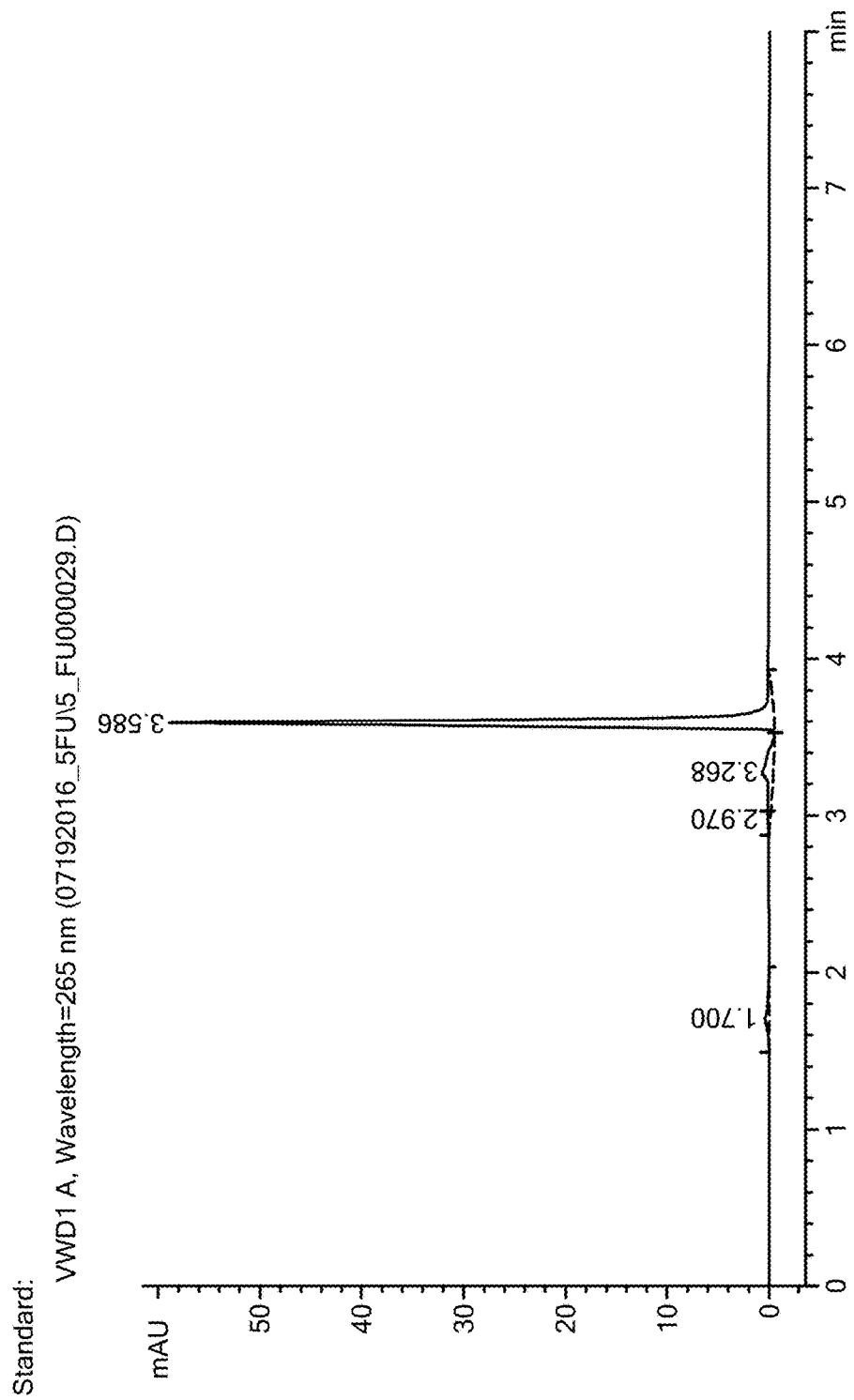
FIGS. 35A-35B show chromatograms monitoring the release of 5-Fluorouracil ("5-FU") from a device including particles loaded with 5-FU in a chitosan matrix according to embodiments of the present invention.
Figure 35B:
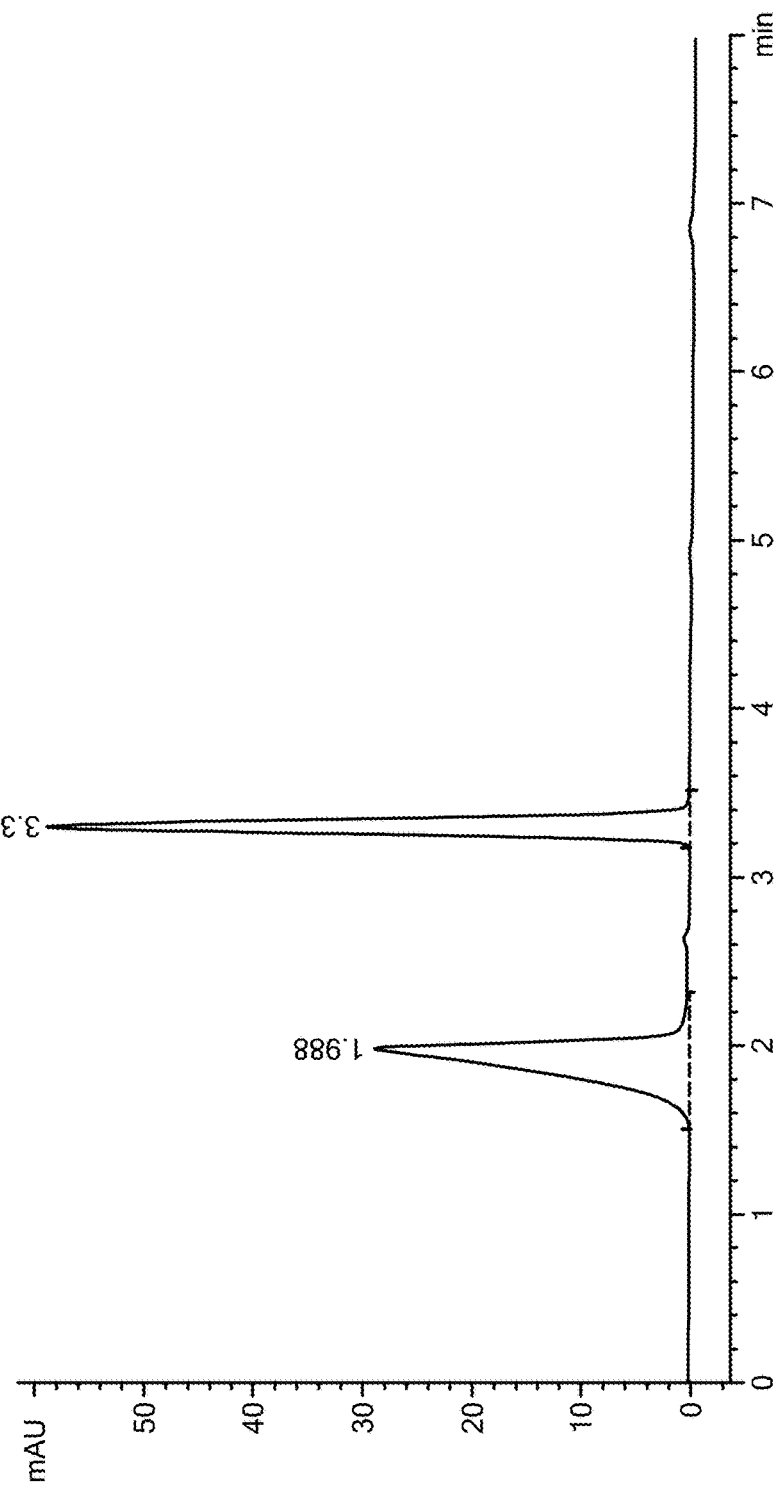

FIGS. 35A-35B show chromatograms monitoring the release of 5-Fluorouracil ("5-FU") from a device including particles loaded with 5-FU and embedded in a chitosan matrix. The particles and matrix, the particles having an average diameter in the range of 500 to 2000 nm, were made with the same procedure and ingredients as the device of FIG. 1, except that this time the particles contained 5-FU instead of cisplatin. The particles where embedded within the matrix to form a particle/matrix device, and the release of 5-FU was monitored via HPLC. The peak at 1.968 is acetic acid contained within the device. Both acetic acid and 5-FU were detectable with ultraviolet light at the 265 nm wavelength emitted by the detector.

In example systems for delivering a therapeutic agent to a site in a mucosal tissue, the matrix has a first and second opposing surfaces. The first surface is configured to be attached to the site in the mucosal tissue, and the matrix is configured to provide controlled release of the microparticles through the first surface. It has been found that release of the microparticles is improved if the second surface is permeable to water. Example water-permeable coatings which may be applied to the second surface include polyacrylate adhesives and non-woven polyester fabrics.

Localized Delivery of Agents Via a Multi-Layered Delivery Device

In one aspect, one or more of the above improvements may be applied to a multi-layered agent delivery device. The multi-layered device is capable of delivering the same or multiple agents in phases over a period of time or delivering multiple agents concurrently via modulation of the makeup of each layer. The device and a method for manufacturing such device have been developed to address the unmet need of delivering agents in a multitude of forms locally to mucosal tissue. The multiple layers within this platform may be used for varying purposes.

Traditional drug delivery to a mucosa consists of an initial bolus dose of agent followed by a steady reduction in exposure over time. This platform is able to mitigate this tendency via its multiple layers and the inclusion of microparticle within at least one layer. The material forming the structure of each layer can be optionally chosen to degrade slowly, and the same agent (such as cisplatin for the local treatment of a cancerous tumor) may be chosen for inclusion within each of the multiple layers.

In one example embodiment, the device therefore can be designed to release cisplatin locally in multiple phases, providing significantly longer treatment without the side effects, multiple doses required or dose limiting hindrances associated with cisplatin that is parenterally administered. The inclusion of microparticles within this device further assists in the device's ability to provide a sustained local dosage. The microparticles included within this device are released once it is applied, permeate the mucosal tissue, and remain local within the tissue beneath which the device was applied. These microparticles then degrade over a period of time, further providing a sustained, longer dosage of agents. When different agents are included within each layer, additional objectives are able to be achieved. For example, if the device is applied for the treatment of a recently acquired open wound, a pain mitigator and anti-infective agent can each be included within a layer.

When applied within the oral cavity, the device is placed directly onto affected oral tissue within the mouth and releases agents for controlled and targeted treatment of oral diseases. Agents which may be included in free form (such as a pain mitigator in the first layer) may be designed to have an immediate effect to the underlying tissue, whereas agents encapsulated within microparticles (such as a chemotherapeutic pharmaceutical) may be included within a second or subsequent layer. The microparticles are then able to act independent of the first agent, permeate the underlying tissue, and provide a sustained, longer term delivery of agent to the tissue. This device overcomes deficiencies of other prior art by offering the ability to modulate the duration and treatment order parameters to provide multiple stages and durations of treatment.

Figure 6:
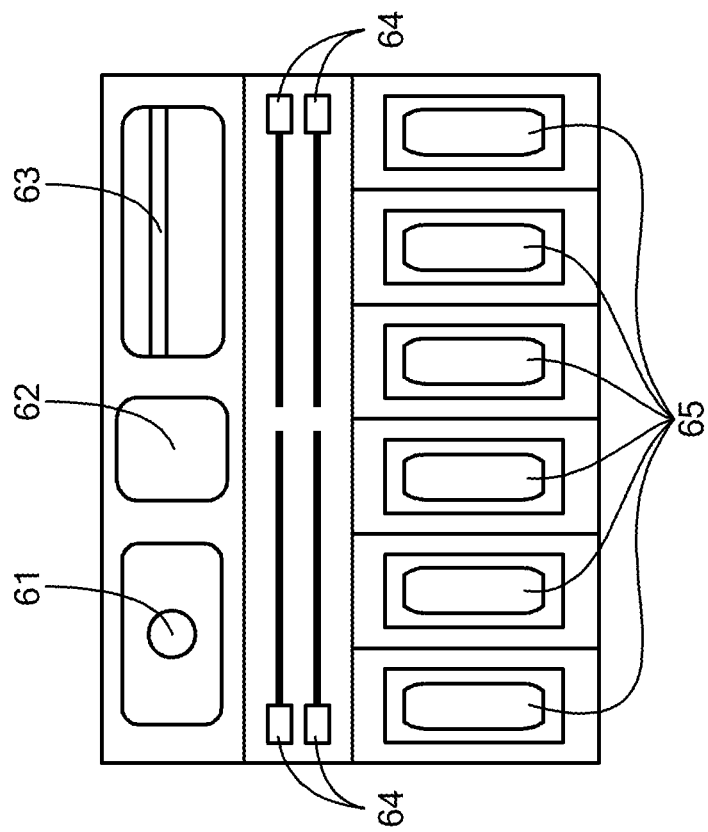
FIG. 6 represents a multi-layer device according to embodiments of the present invention included as part of a treatment kit for use in mucosa-based indications according to embodiments of the present invention.

In addition, the device may be further included within a treatment kit to optimize its safety and efficacy. The kit can be optimized for a mucosa. FIG. 6 represents an example multi-layer device included as part of a treatment kit for use in mucosa-based indications. The figure illustrates a kit containing six treatment devices, where: 61 refers to a wetting agent or permeation enhancer which may be externally applied to the mucosa prior to treatment (in either solution or powder form), 62 refers to gauze or other similar absorbent pad which may be used to moisten and keep the device in place within the oral cavity, 63 a bag for disposal of hazardous waste (for use when hazardous agents are included or otherwise), 64 identifies forceps or forceps-like devices used to keep the device in place and to prevent swallowing, and 65 refers to six individually packaged and stored treatment devices.

The release of agent(s) from the device is activated in part by exposure to moisture. Therefore, a moisturizing solution such as saline may be provided with the device to be used during the application process. Further, permeation enhancers in powder or solution form may be included to be externally applied to the mucosa prior to application of the device. The permeation enhancer may optionally be included in the form of a powder which requires reconstitution. The powdered form may be included to maintain stability of the permeation enhancer. When included in this form, the kit may optionally include additional materials among which at least one glass vial (5 mL to 20 mL in size) containing sterile water to be used for reconstitution. The kit may additionally include syringes (such as 3 mL Luer-lock syringes) and aspirating needles (such as 18 G needles) to be used for reconstitution of the permeation enhancer.

In addition, when the device is used for certain indications (such as oral indications), care must be taken to ensure that the product is safely applied and removed to prevent choking or swallowing. The kit disclosed herein addresses these concerns by including all materials necessary to ensure the safe application device. Example kits include at least one pair of forceps (either multi-use metal forceps or single use disposable plastic forceps) or other similar instrument used to position and place the device to prevent exposure of agents to people or exposure of the device to the throat.

Disposable packaging can also be included within the kit to ensure the safe disposal and non-contamination of the treatment process by isolating the materials used during treatment. This packaging may include a hazardous waste package used when toxic drugs such as those used to treat oral cancer or melanoma are administered, or biohazard packaging. Additionally, empty scintillation vials may be included to collect the used device post-treatment for purposes such as residual-agent analysis.

Figure 2:
FIG. 2 is an image of a multi-layered device according to embodiments of the present invention. The device features two layers: one top layer including FITC, a fluorescent dye which fluoresces green when examined under a fluorescent microscope, and one bottom layer including Cy5, a fluorescent dye which fluoresces red when examined under a fluorescent microscope.
Figure 3:
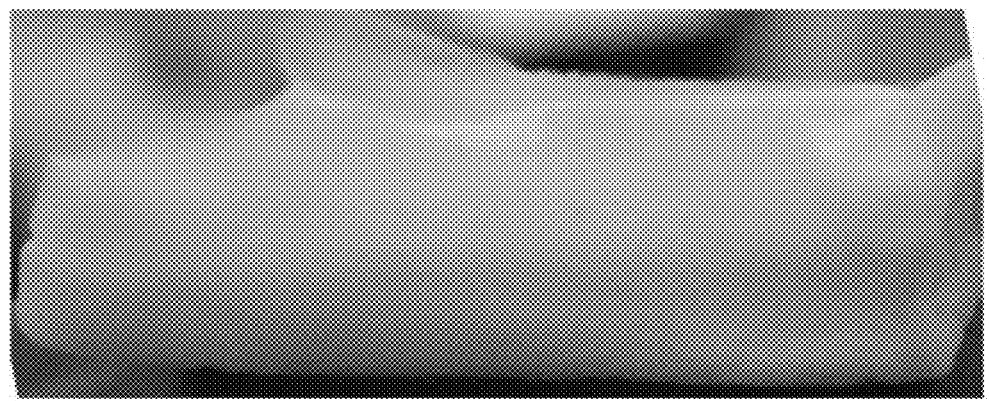
FIG. 3 represents another multi-layered delivery device according to embodiments of the present invention. The pictured also features two layers: one "lighter" top layer containing 5-fluorouracil, a chemotherapeutic, and one "darker" bottom layer containing cisplatin, another chemotherapeutic.

In representative embodiments, a method of manufacturing of a multi-layered device and a formulation created according to such method are provided, as shown in the non-limiting examples of FIG. 2 and FIG. 3). The method includes the freezing and freeze drying of polymeric solutions containing a therapeutic agent.

Precursor mixtures are first created, then subjected to freezing or freeze drying. The device may feature multiple layers, as illustrated for instance in FIG. 2 and FIG. 3, and the precursor mixture to each layer may be separately made. All layers may each contain an independently chosen agent to be delivered, and at least one layer contains microparticles which further encapsulate at least one of the agents. The microparticles may be synthesized, for instance, according to the ionotropic gelation method, where no modification of the agent takes place. Microparticles are designed to range from 200 to 2000 nanometers, more preferably 500 to 2000 nanometers, and yet more preferably from 500 to 1000 nm in average diameter. Agents such as a permeation enhancer, taste masking elements and agents for the formation of body structure may be added. These agents may include propylene glycol, hydroxypropylmethylcellulose, chitosan, sweeteners, peppermint or other flavorings, among many others. Solutions containing agents but no microparticles may also contain these and other agents.

Once ready, the precursor mixtures are subjected to freezing. It is preferable that the layers of the device be first frozen in a freezing bath of an aqueous alcohol at a temperature of at most −40° C., for example in a bath of aqueous ethanol and dry ice. This method has been found to result in a device which is able to release nearly all of its agent content and permeate deeply into the desired mucosal depths. Without wishing to be bound to any particular theory, the product device is more effective as compared to other methods of freezing. When the precursor mixture was frozen via liquid nitrogen, placement in a freezer at −80° C., or standalone dry ice, some of the microparticles burst and the polymer in the matrix of the device became more rigid, resulting in a low percentage of agent release and a compromised therapeutic efficacy. For best results, the bath should include dry ice completely covered by a solution of at least 90 wt % ethanol in water. The precursor mixture of the first layer of the device (in liquid form) is poured into a mold, for example a silicone molding and is submerged approximately ⅔ to ¾ in the bath of ethanol and dry ice, to form a frozen layer. Preferably, thirty minutes should be allowed to achieve complete freezing.

After freezing the initial layer, a second layer may be added by one of two methods. In the first method, the precursor mixture of the second layer is poured in liquid form on top of the frozen first layer while the first layer remains in the ethanol/dry ice bath. The resulting frozen bottom layer and liquid top layer are then submerged more deeply until a ⅔ to ¾ overall submersion ratio is met. Another 30 minutes are allowed for complete freezing of the second layer. Subsequent layers in excess of two may be added by the same process.

In the second method, each layer is separately and concurrently frozen in its individual mold within the freezing bath. After thirty minutes are allowed to ensure complete freezing of each layer, a coating of an solution of one or more salts, for example 0.12% saline, is brushed onto the first, initial layer. Within about a minute of the application of the coating, the second layer is applied onto the first and a pressure of about 0.25 kg is applied. This results in a combined solid. Subsequent layers in excess of the second layer can be applied by the same method.

After all the desired layers have been added, the device is moved into a lyophilization chamber for about one to three days, depending on the number of devices loaded into the chamber. After the lyophilization removes all liquids, the multi-layer device is ready for use, as illustrated in the examples of FIG. 2 and FIG. 3.

In one representative embodiment, a multi-layered device may be used for the delivery of multiple agents over a concurrent period of time. For example, if use for the treatment and pain mitigation of mucositis is desired, one layer may include a pain mitigator, and one layer may include an agent for the treatment of mucositis.

Figure 4:
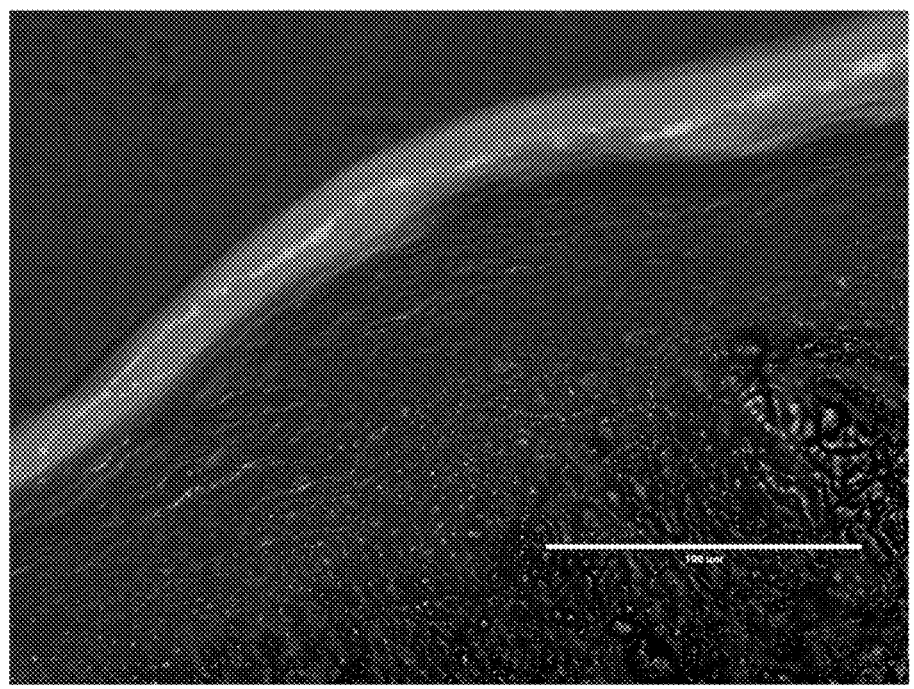
FIG. 4 is a microscope image taken from oral buccal tissue. The red light is from the Cy5 fluorescent dye and the green light is from the FITC fluorescent dye.
Figure 5A:
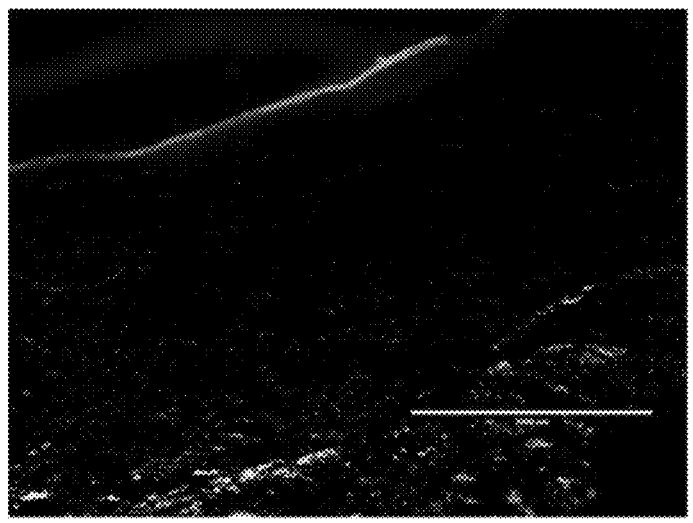
FIGS. 5A-5C show three images taken from lamb buccal tissue at different time points.
Figure 5B:
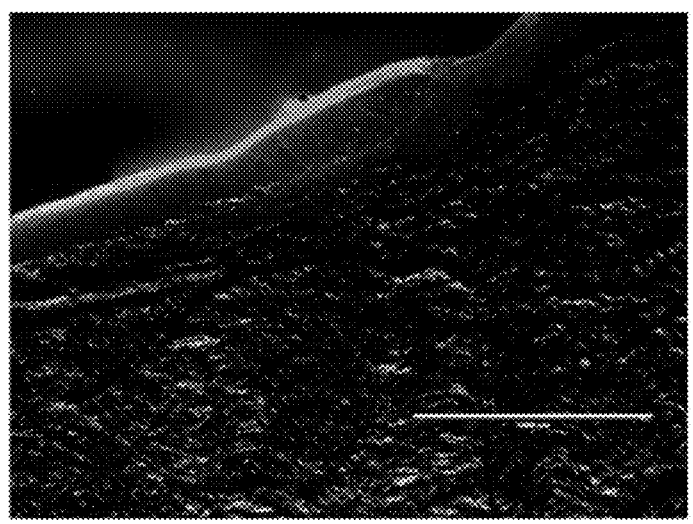
Figure 5C:
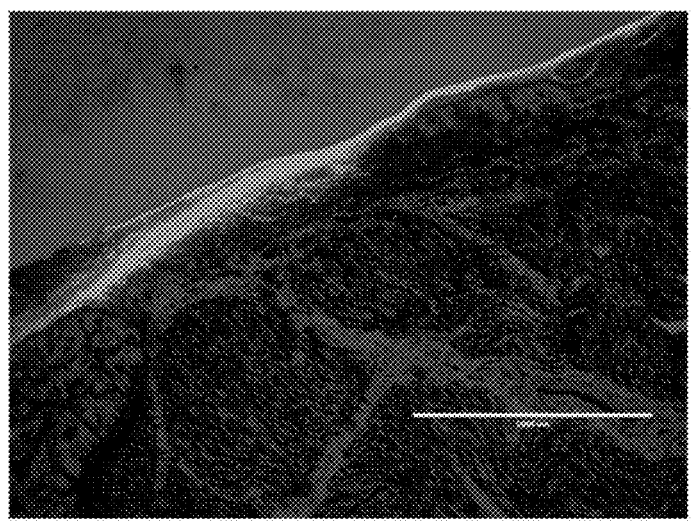

In another representative embodiment, a multi-layered device may be used for the delivery of multiple agents over a prolonged period of time (FIG. 4, FIG. 5). If the example of mucositis is again used, multiple layers may include a pain mitigator in free form, a pain mitigator encapsulated within microparticles and an agent for the treatment of mucositis encapsulated within microparticles. The initial freeform layer is able to provide immediate pain relief, and the subsequent particle-encapsulated layers are capable of delivering microparticles beneath the tissue, where they further release their agents over a period of days, providing longer-term pain relief and treatment. FIG. 4 and FIG. 5 illustrate this effect. Fluorescence was used in order to provide detection. As shown, the multiple fluorescent layers released over time and permeated the tissue at different rates, providing a customized treatment.

Kit for the Treatment of Oral Cancer and Other Oral Diseases

In another aspect, a kit, including a local drug delivery device within the mouth and materials for its successful administration and subsequent disposal is provided. This kit is specifically designed to provide the proper tools and treatment device required to deliver agents into oral tissue to treat oral diseases. Targeted delivery within the mouth into the oral tissue is desired. The motivation behind the development of this kit has been to treat the severely underserved market pertaining to untreated or poorly treated oral diseases.

One of the preferred embodiments of the kit delivers a safer and more effective oral cancer treatment locally into the oral tissue. In this embodiment, the active drug is included within a treatment device, which is in turn included in the present kit. The kit also includes a number of elements to ensure a safe treatment process for both clinicians and patients, such as thorough proper handling, disposal, and storage of the treatment device, as well as at least one permeation enhancer. At least a fraction of the active drug within the treatment device is encapsulated within mucoadhesive microparticles, which leads to local retention of the drug within the oral tissue. As a result, only a fraction of the chemotherapeutic is required, but the local targeting enables a more concentrated dosage at the tumor location compared to all traditional treatment options. An application via this kit can result in the significant reduction of side effects, more effective treatment, elimination of debilitating surgery and recovery, and a safer overall treatment.

The improvements of this kit over traditional treatment devices are in part based upon the administration, disposal, storage, and/or packaging requirements of the treatment device. In certain embodiments, highly sensitive and potent chemotherapeutics are contained within the treatment device. Proper handling procedures must be followed to prevent exposure of the chemotherapeutic to clinicians, or improper application to patients. Materials which set out these proper handling procedures may be included with the kit. Proper disposal of the treatment device following administration may be essential to prevent potential contamination or exposure. Procedures to wash the treatment location within the mouth both before and following administration may be necessary and therefore proper materials for that purpose must also be supplied. The treatment device must also be packaged appropriately as many chemotherapeutics and the treatment device are sensitive to light and humidity. Packaging must be included for the device and will preferably be made of pharmaceutical grade materials. There may also be a small protective insert of plastic where the wafer is held within a small plastic cup sealed in a pouch. There may also be materials such as Luer-lock syringes, aspirating needles and sterile water to be used for reconstitution of the permeation enhancer (if provided in powder form).

These improvements are conducive to forward the commercialization of the device and kit disclosed herein. The improvements also protect the safety of operators from the agents included within the treatment device and the patient from improper administration, which could result in the accidental swallowing of the device. The use of additional components within the kit also facilitates higher compliance rates among patients, and consequently a greater number of successful treatments. Proper preparation and cleaning of the application area will also prevent irritation to the oral tissue.

Oral mucositis is also a significant disease due in part to the fact that it can occur in the mouth when systemic chemotherapy is given for any reason, not only oral cancer. In a second embodiment, the treatment device within the disclosed kit may include agents which treat or relieve pain, or otherwise address oral mucositis. Unlike existing treatments for mucositis, the current kit includes a device which contains agent-encapsulated microparticles within it. In a manner similar to its effect treating oral cancer, the microparticles released from the device are mucoadhesive so that they remain local to the site of the mucositis. Since the particles are nanoscale, they are able to permeate the tissue and release the encapsulated agent deeper within the affected area than other current treatments, and without broader exposure of the agent. Administration via this kit is able to offer a much more effective delivery of agents to areas affected by mucositis.

In another embodiment, the described kit is also used to deliver agents for the treatment of precancerous/premalignant oral lesions. Precancerous/Premalignant lesions are often left untreated when detected due to a lack of ideal treatment options. A diagnosis is often coupled with monitoring for malignancy rather than early treatment because chemotherapy or surgery can be considered too extreme for early lesions. It is also difficult to differentiate between precancerous/premalignant lesions and other non-malignant lesions. For this reason, there often exists an unwillingness to administer damaging systemic chemotherapy for a potentially non-life threatening issue. To address these conditions, the present kit can be used to administer lower dosages of chemotherapeutics or other agents to these lesions. Treatment would be able to be administered on a much larger scale due to the higher efficacy achieved with such a small dosage and the significantly higher safety. For these reasons, the present kit is viewed as a significant improvement and viable alternative to current treatment methods. Furthermore, the inclusion of the treatment device within a kit is also viewed as a significant improvement over U.S. application number US 2014/0234212 in which the treatment device alone is disclosed due to the safety and efficacy reasons described above.

In representative embodiments, the kit includes a mucoadhesive drug delivery device containing active agent-encapsulating microparticles and items useful for the successful administration and disposal of the device, such as: an oral permeation enhancer either incorporated within the delivery device or provided within the kit alongside it, and an oral rinse used to cleanse the mouth prior to or following treatment.

Figure 7:
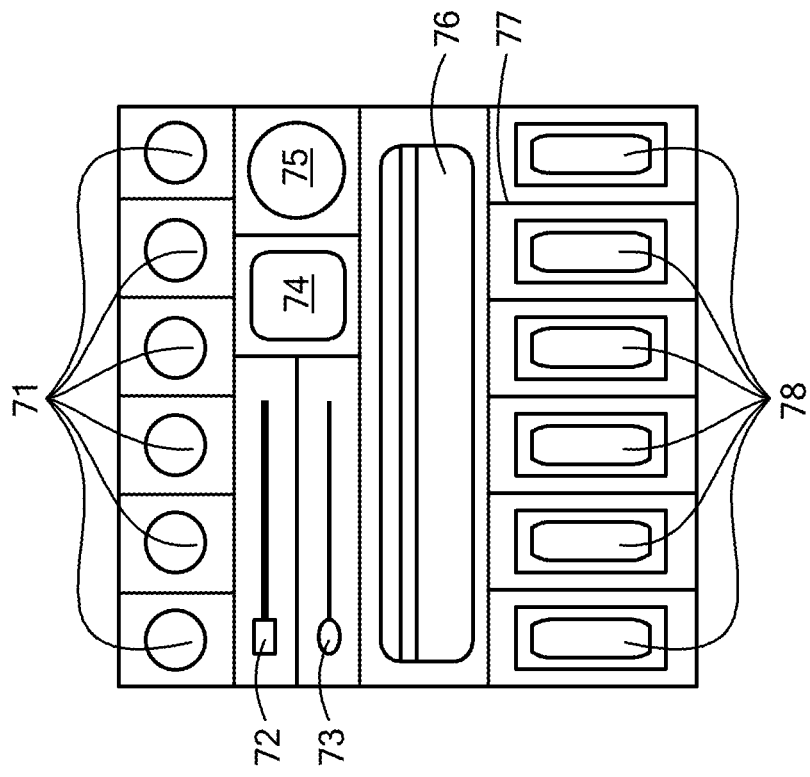
FIG. 7 is a schematic depiction of a kit containing 6 treatment devices according to embodiments of the present invention.

FIG. 7 is a schematic depiction of a kit containing 6 treatment devices, where: 71 refers to individual containers of permeation enhancers (in either solution or powder form), one applied for each treatment, 72 forceps or forceps-like instrument used to apply the treatment device, 73 cotton/sponge tipped applicator used to apply the permeation enhancer, 74 gauze or other absorbent pad to be used during treatment, 75 container of mouth rinse, some of which will be used during each treatment, 76 Disposable packages for the remainder of device and other waste generated during application, 77 identifies the structural sides within the kit that separate the materials from one another, 78 six individually packaged and stored treatment devices.

Figure 8:
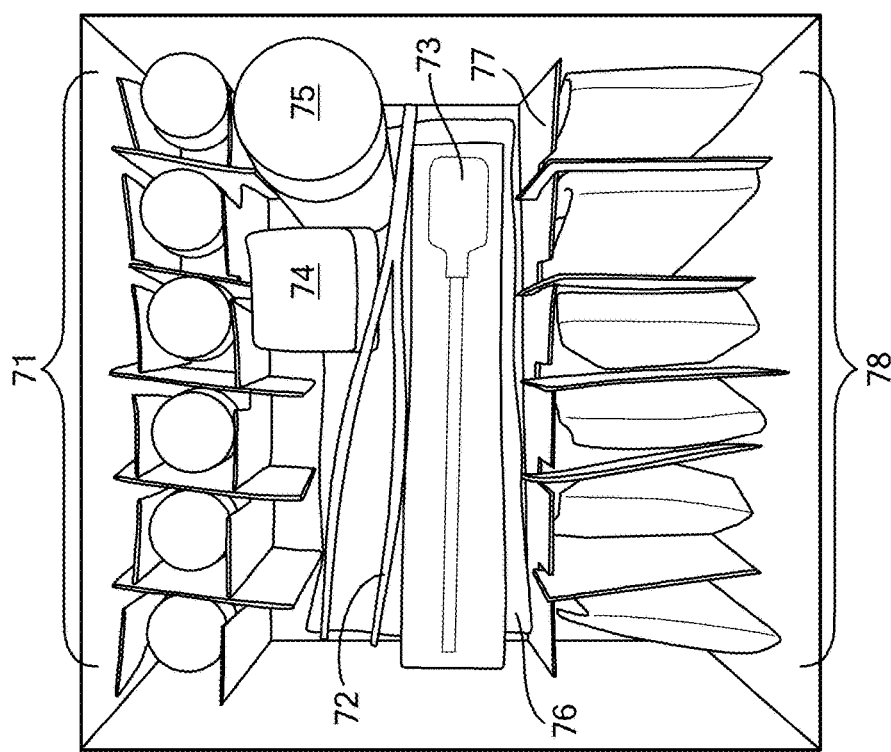
FIG. 8 is an image taken of one of the treatment kits designed in accordance with the depiction of FIG. 7.

FIG. 8 is an image taken of one of the treatment kits, designed in accordance with the depiction of FIG. 7.

Figure 9:
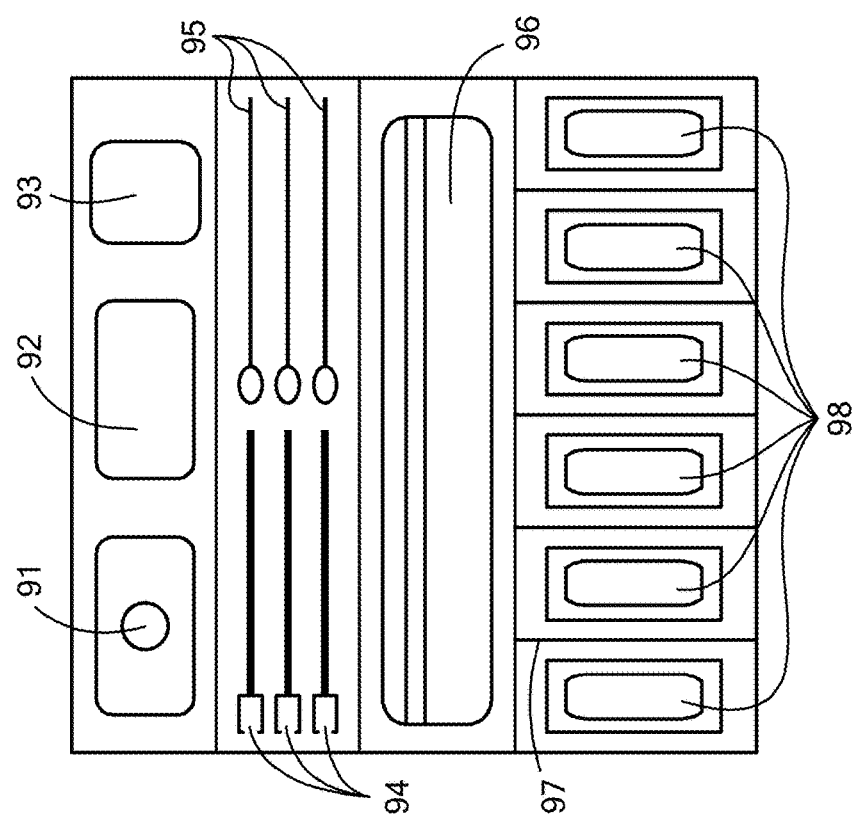
FIG. 9 is another schematic representation of a kit according to embodiments of the present invention.

FIG. 9 is another schematic representation of a kit, which includes: 91 one container of permeation enhancer which is utilized during all 6 treatments (in either solution or powder form), 92 the oral mouth rinse used during each treatment, 93 gauze pad or other absorbent material used during treatment, 94 disposable forceps or forceps-like devices used during treatment to place and remove the treatment device, 95 multiple disposable applicators used to apply the permeation enhancer during each treatment, 96 Disposable packages for the remainder of device and other waste generated during application, 97 identifies the structural sides within the kit that separate the materials from one another, 98 six individually packaged and stored treatment devices.

Targeted Gastrointestinal Delivery of Agents

In another aspect, a disclosed particle-based agent delivery system has been developed for the treatment of gastrointestinal diseases and conditions. The delivery device disclosed herein is in part effective because of its ability to adhere to the intestinal mucosa.

The properties of mucus itself must first be understood to properly develop a delivery system. Mucus is a viscoelastic gel layer that protects tissues that would otherwise be exposed to the external environment. Mucus is composed primarily of crosslinked and entangled mucin fibers secreted by goblet cells and submucosal glands. Mucins are large molecules, typically 0.5-40 MDa in size, and coated with a complex and highly diverse array of proteoglycans. Mucus pH can vary greatly depending on the mucosal surface, with highly acidic environments capable of aggregating mucin fibers and greatly increasing the mucus viscoelasticity. In the human GI tract, the mucus layer is thickest in the stomach and the colon. Gastric mucus is exposed to a wide range of pH: a large pH gradient exists within the same mucus cross-section, with pH rising from the luminal pH of 1-2 to 7 at the epithelial surface.

Accordingly, provided herein is a gastrointestinal drug delivery system capable of modulating the release of agents depending on the environmental pH, thereby making possible the specific targeting of drugs within the gastrointestinal tract. Described herein are efforts to target drug delivery to the gastrointestinal tract through the design of a mucoadhesive delivery system which releases its payload only within the pH environment of the gastrointestinal (GI) tract, and, more specifically, to specific regions within the GI tract. Because of the mucous lining of the GI tract, attraction to the mucosa and mucoadhesivity are important elements of this device.

In the case of orally administered agents for gastrointestinal delivery, survival through digestive regions of extreme pH values is necessary. In the human stomach, the volume of gastric fluid ranges from 20 to 100 ml with a pH of 1.5-3.5. Gastric fluid consists of hydrochloric acid, potassium chloride and sodium chloride. Fluid secretion takes place over several stages. Hydrogen and chloride ions are secreted and mixed in the canaliculi. The lumen of the oxyntic gland secretes the gastric acid which reaches the stomach lumen. Secretion of the chloride and sodium ions creates a negative potential of approximately −35 to −65 mV, which allows for diffusion of the potassium and sodium ions from the cytoplasm.

Carbonic anhydrase forms carbonic acid by catalyzing reactions between water and carbon dioxide. This allows for the dissociation into hydrogen and bicarbonate ions. The hydrogen ions then move from the cell. Sodium ions are reabsorbed. In the canaliculus, hydrogen and chloride ions mix and are secreted into the lumen of the oxyntic gland.

Gastric acid production is separated into three phases. The first of these is the cephalic phase, where approximately 30% of gastric acid production is stimulated by the smell, taste, or expectation of food as signaled by the brain. About 50% of gastric acid is produced during the gastric phase, where stimulation of production occurs by food presence in the stomach and release of amino acids from consumed materials. The intestinal phase represents the last phase of acid production, where the remaining 20% of acid is produced when chyme (semifluid of partially digested food) enters the small intestine. If agents targeted to the gastrointestinal mucosa are to be delivered orally, the delivery system must remain intact and stable through the gastric acid of the stomach. Through the development of a system which is able to remain stable in this environment as well as multiple pH conditions, oral administration for delivery of an agent into and within the gastrointestinal mucosa is made possible. As opposed to traditional products with an enteric coating, this system is both able to withstand a multitude of pH levels as well as contain a combination of particles which are able to release in desired pH conditions.

In order for orally administered alternatives to enteric capsules to be efficacious in the treatment of gastrointestinal diseases, such alternatives should possess the capability of remaining stable throughout the entire described acidic and dynamic stomach digestion process. Likewise, since many GI diseases may encompass multiple regions of the GI tract that span multiple pH ranges, the development of a delivery system that is able to withstand and release over various pH changes is advantageous. An efficacious alternative should also be characterized by the ability of becoming attracted by means of mucoadhesivity to the intestinal mucosa lining and releasing upon contact or at a designated time thereafter. Thus, provided herein is a therapeutic, diagnostic and/or prophylactic delivery device for local and systemic administration and delivery into the gastrointestinal stem cells and/or systemically beyond, which is able to become attracted/attach to and penetrate through the intestinal mucosa as well as remain stable in acidic stomach conditions. The devices described herein are able to provide an extended or delayed release, programmable release, and site specific release into and within gastrointestinal locations.

In many instances, oral administration is not possible if the patient is unable to swallow a capsule or tablet. This can occur with young children where compliance is low or among the elderly where pain exists or there is otherwise an inability to take oral medication. People with feeding or nasogastric tubes are other examples of these cases. It is therefore an additional object of some embodiments of the present invention to provide a method of oral delivery of agents to patients who otherwise would be unable to be administered oral agents. This is in part accomplished through the optional use of liquid and gelatin forms of oral administration for those who cannot swallow solid tablets or capsules, as well as through nasal administration or consumption through a nasogastric or feeding tube. Compared to traditional administration techniques, the delivery system provides for the successful delivery through theses avenues. Particles may be provided in a variety of forms and tailored to specific needs.

The gastrointestinal delivery system also provides a therapeutic, diagnostic and/or prophylactic delivery device that is effective in the presence or potential presence of gastrointestinal fluids, in contrast to the traditional washout problems described above associated with such fluids. Also provided is a route for administering a therapeutic, diagnostic and/or prophylactic agent to one or multiple specific regions of the intestinal epithelia through the design of a system containing one or more sets of particles able to withstand and release through a multitude of pH ranges.

For these and other purposes, the gastrointestinal delivery system disclosed herein may serve as a device for specific, targeted delivery within the gastrointestinal tract to the gastrointestinal mucosa. In exemplary embodiments, the delivery device adheres to the gastrointestinal mucosal tissue, is able to withstand the low pH, acidic environment of the stomach and contains pH-targeted, mucoadhesive particles in which one or more agents are encapsulated. The device may also include permeation enhancers sufficient to facilitate agent permeation through the mucosal layer of the gastrointestinal tract.

One of the unique properties of this platform is that the release and targeting attributes can be controlled based on desired parameters. The particles may be controlled to remain stable within a desired pH level and release in another desired pH level. This ability may be used to create a combination of targeted particles which can remain stable through any component of the GI tract regardless of pH exposure, including the stomach, esophagus, and components of the intestines.

In addition to stability, the timing of release of the agents encapsulated within the particles may be controlled. The purpose of this feature is to further target the delivery to locations within the GI tract. For example, if it is known that under normal digestion conditions, a known amount time is known to intercur between oral consumption and delivery to the desired delivery, the particles within the delivery system may be further designed to release their agent payload at such amount of time after oral contact is made with the delivery system. A formula has been developed by which the release time may be determined. The parameters and formula are identified below:

Degree of Deacetylation (DA)
Molecular Weight (MW) combinations,
Time (T)
Amount of exposure to humidity, water content (WC)
Solution pH (SpH) at the synthesis stage
Degree of Viscosity (DV)
Synthesis technique (K is a constant) such as freezing method of the particles Formula: Degree of release $(DR) = a(DA) + b(MW) + c(SpH) + d(T) + e(WC) + f(DV) + k$ It has been discovered that the use of sodium nitrite allows for further modulation of the degree of deacetylation and molecular weight of chitosan.

Figure 10:
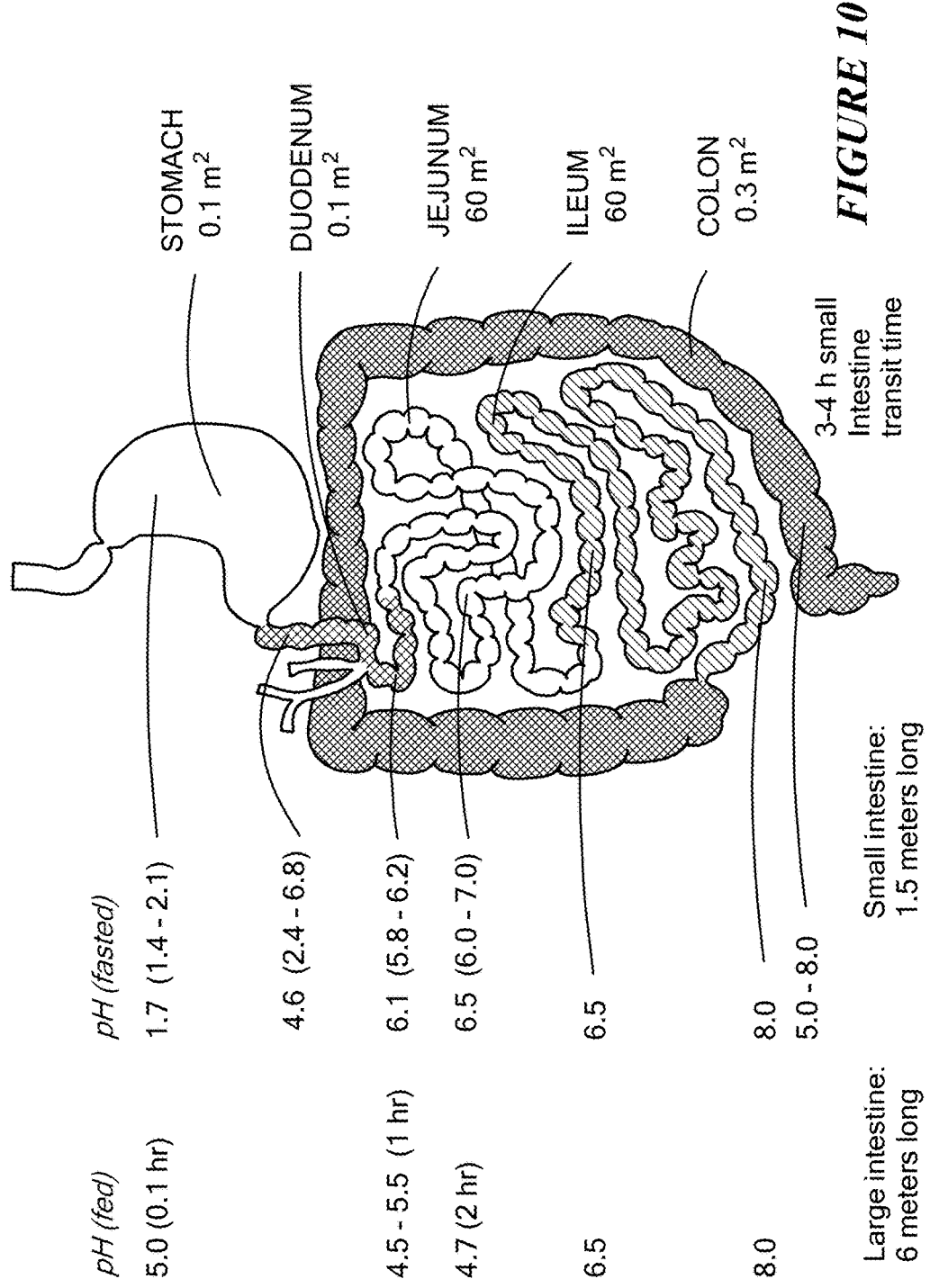
FIG. 10: Illustration of the human GI tract from the stomach onwards and associated pH levels of each region.

The pH modulation and configurable release timing increases the efficacy of the delivery system and shows how innovative it is compared to traditional systems. Without wishing to be bound to any particular theory, it is believed that such superior properties are the product of previously unknown effects of the degree of deacetylation and molecular weight of the chitosan. FIG. 10 shows the pH levels of a portion of the GI tract. Using this information and the relationship between pH and location, delivery can be targeted. For example, particles can be programmed to release at pH levels of only between 5.8 and 6.2, thereby making possible the specific targeting to the duodenum.

Figure 11:
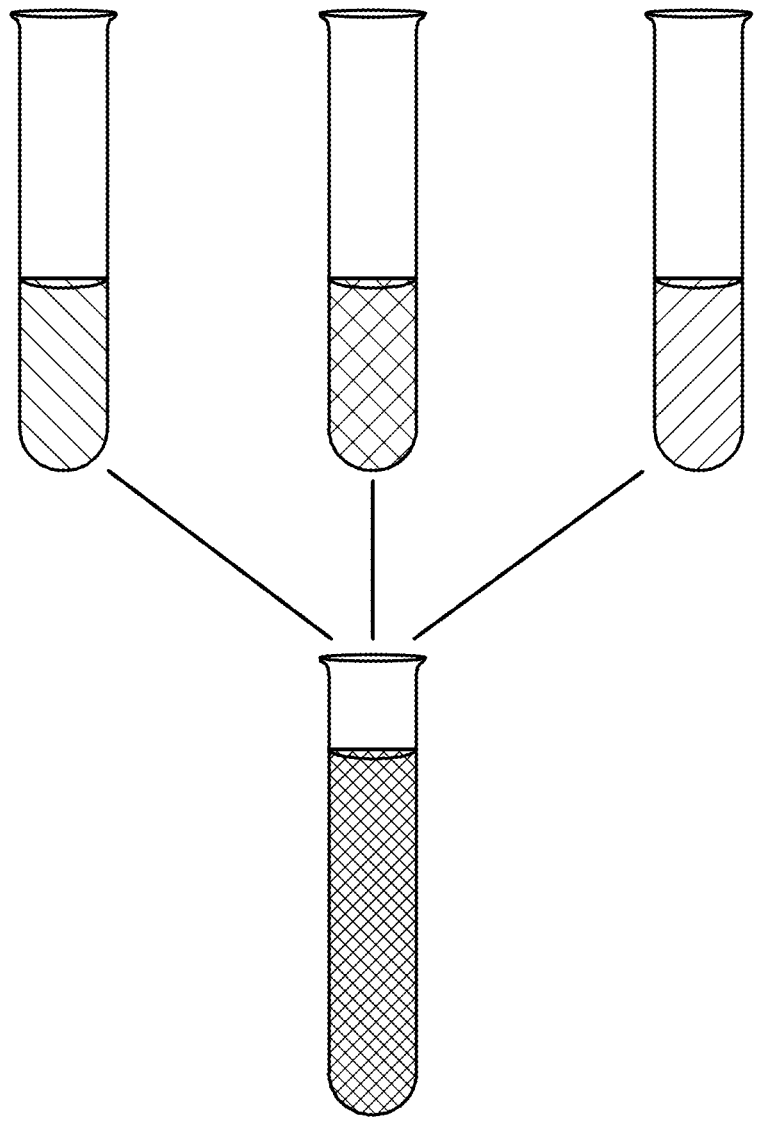
FIG. 11: Depiction of how solutions containing particles ("Ps") with different properties can be combined to offer targeting to multiple exclusive regions within the GI tract according to embodiments of the present invention.

Targeting release to multiple locations can be achieved by the inclusion of a blended mix of customized particles within the delivery system. An example of this application is shown in FIG. 11. This allows for targeting to an array of desired locations if a disease or condition is located in multiple regions, or if an agent is best delivered over a range of locations.

I. Agent Delivery Device

Figure 13:
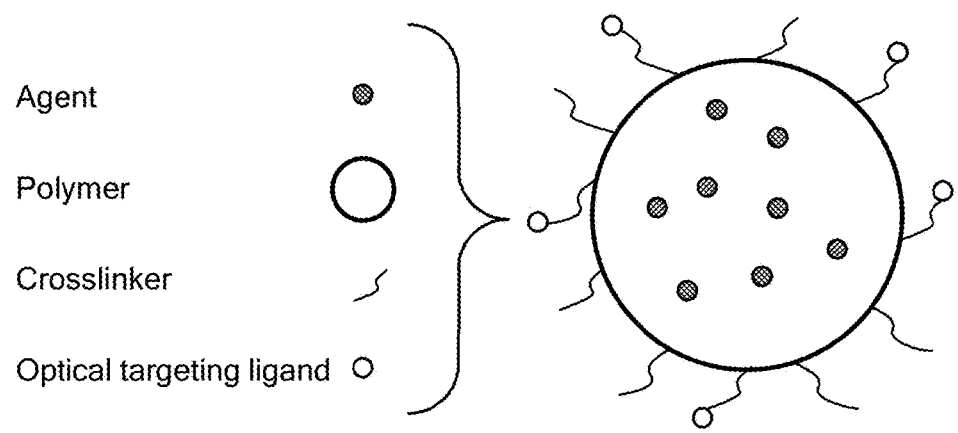
FIG. 13: A depiction of a particle containing an active agent according to embodiments of the present invention. As the image illustrates, targeting ligands, crosslinkers, agents, additional polymers and combinations may be included within the particles.

The device includes agent-encapsulating particles consisting of a polymer having dispersed or encapsulating therein a therapeutic, prophylactic, diagnostic or nutraceutical agent (FIG. 13). If desired, the particles may include chemical linkers, which can couple targeting ligands and/or additional agents to the particles (FIG. 13). The device includes these particles as well as preferably permeation enhancers.

Figure 12:
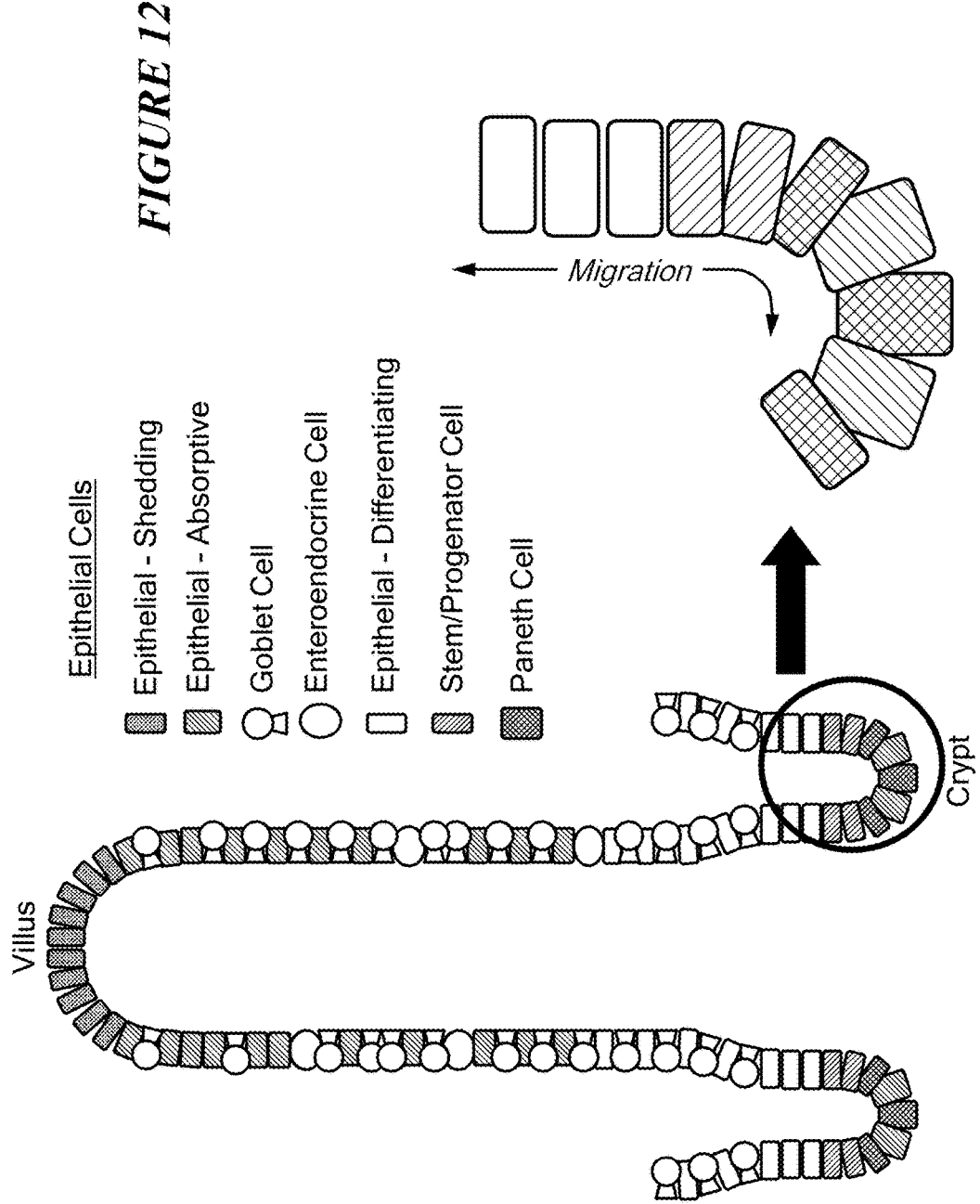
FIG. 12: Graphical depiction of epithelial cells and the location of crypts, which are one of the targeted areas the disclosed concept.
Figure 16:
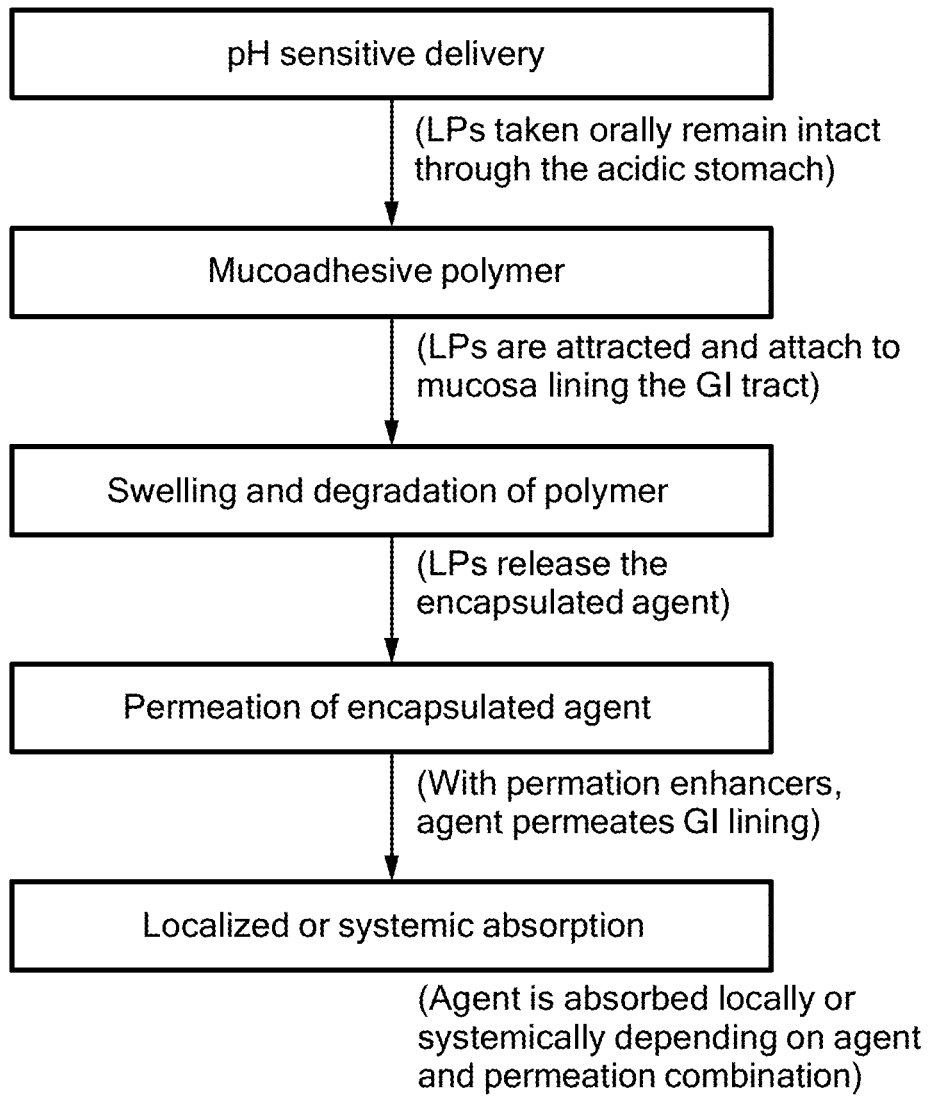
FIG. 16: A graphic chart illustrating the delivery and absorption process according to embodiments of the present invention.
Figure 17:
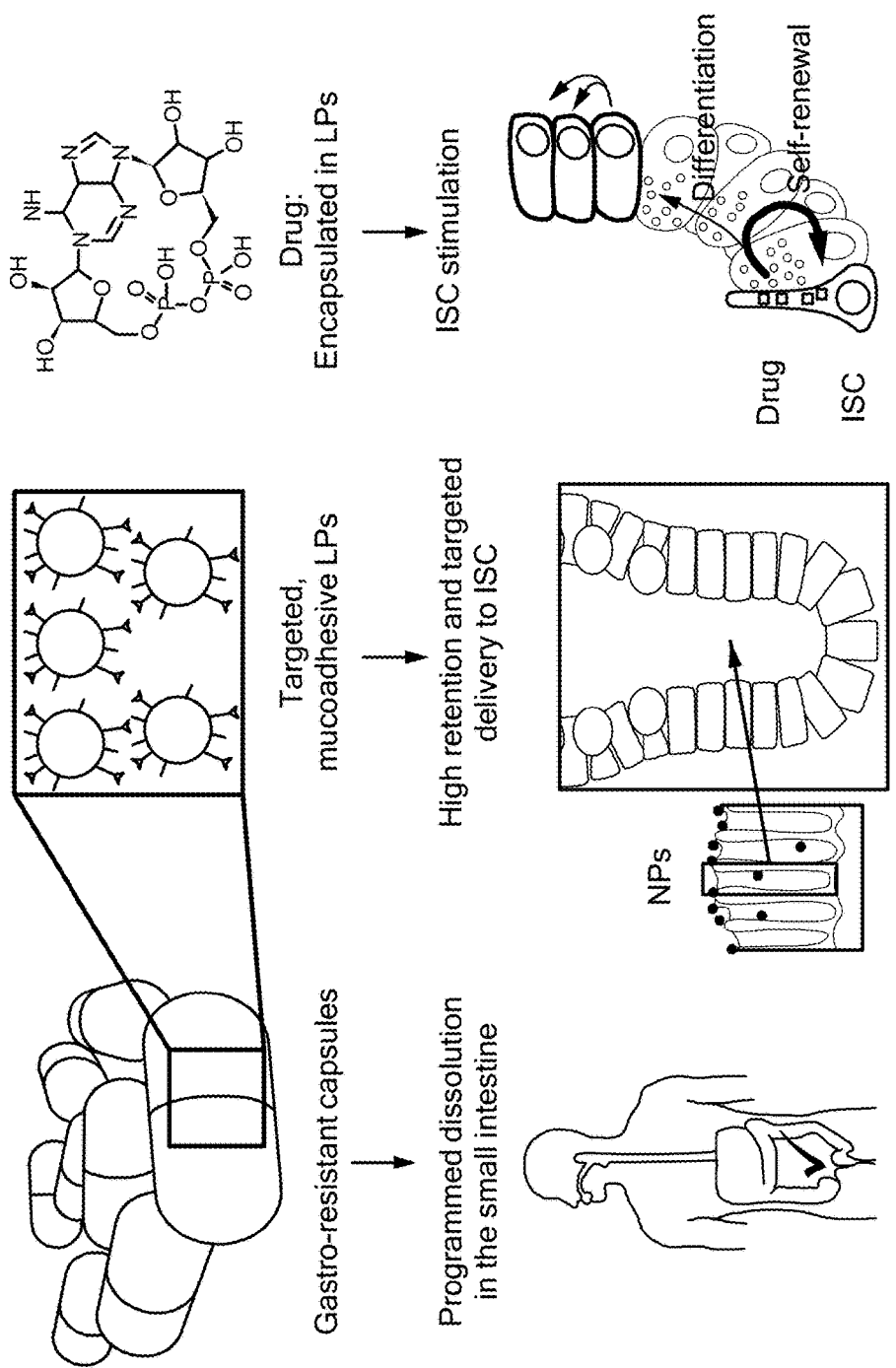
FIG. 17: Illustration depicting how, according to embodiments of the present invention, enteric capsules may be used to target intestinal stem cells.
Figures 18A, 18B, 18C:
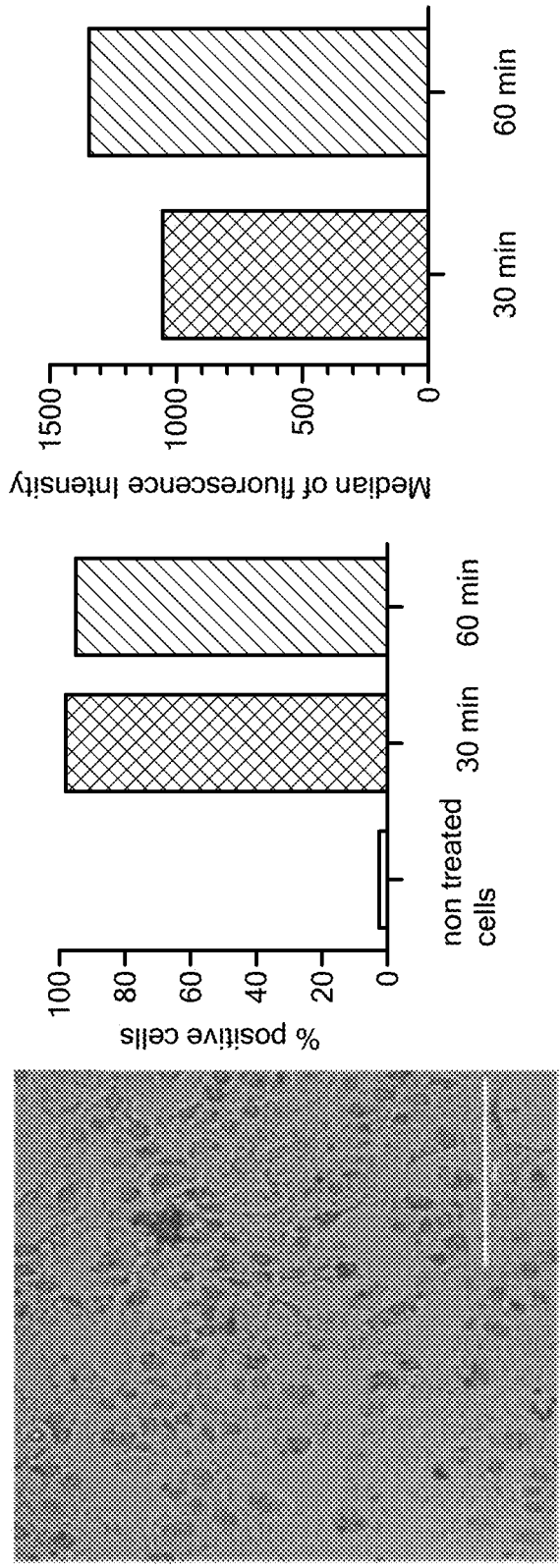
FIGS. 18A-18C: Data from a cell uptake study, including a microscopy image 1 hour after incubation with Alexa 647 particles (FIG. 18A). Evaluation of cell uptake by flow cytometry, percentage of positive cells after 30 and 60 min incubation with particles at a concentration of 0.03 g/L (FIG. 18B). The results showed that particles were taken up by more than 95% of the cells in both cases
Figure 19:
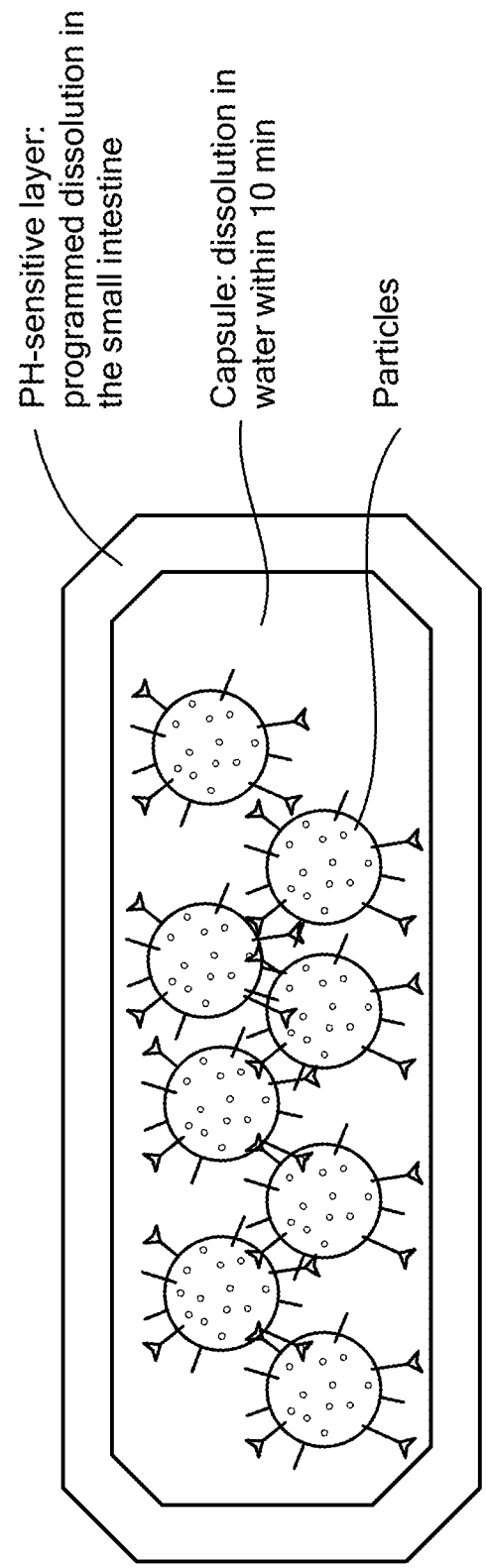
FIG. 19: Image showing how the design of enteric capsules would include and protect particles.

The device may be orally administered via tablet, capsule, liquid, syrup, gelatin or other oral consumable, or via nasogastric tube or feeding tube for those who are unable to swallow, and exhibits properties which allow the agent encapsulated in the particles to remain stable in the variably acidic environment of the stomach. The device is able to deliver agent-encapsulated particles ("loaded particles", also labeled as "LPs") to the epithelial cells within the gastrointestinal (GI) tract (FIG. 12). The particles adhere to the intestinal mucosa and degrade, releasing the encapsulated agent directly into the intestinal epithelium. FIG. 16 illustrates the drug delivery process.

Figure 14:
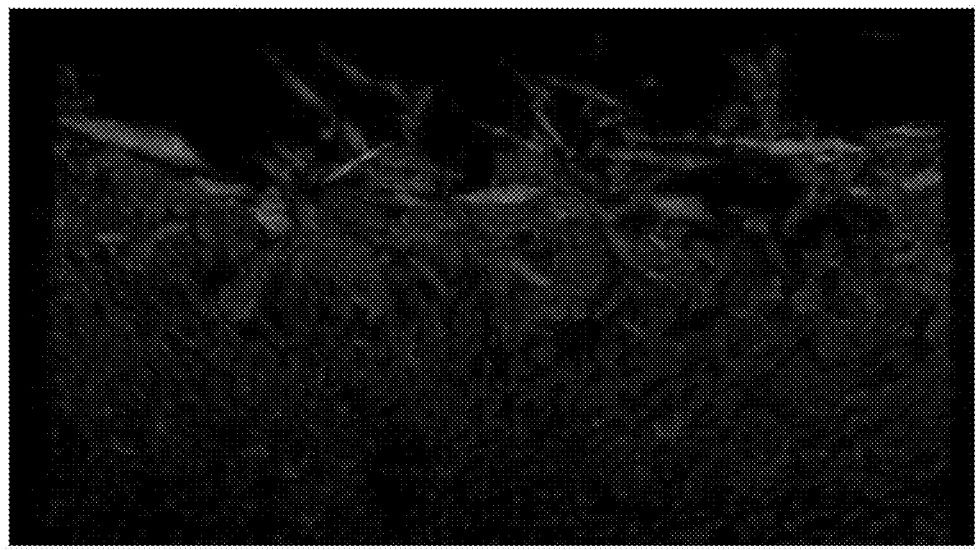
FIG. 14: ATTO (Red fluorescent dye) labelled particles according to embodiments of the present invention permeating into and beyond the basement membrane of intestinal mucosa.
Figure 15:
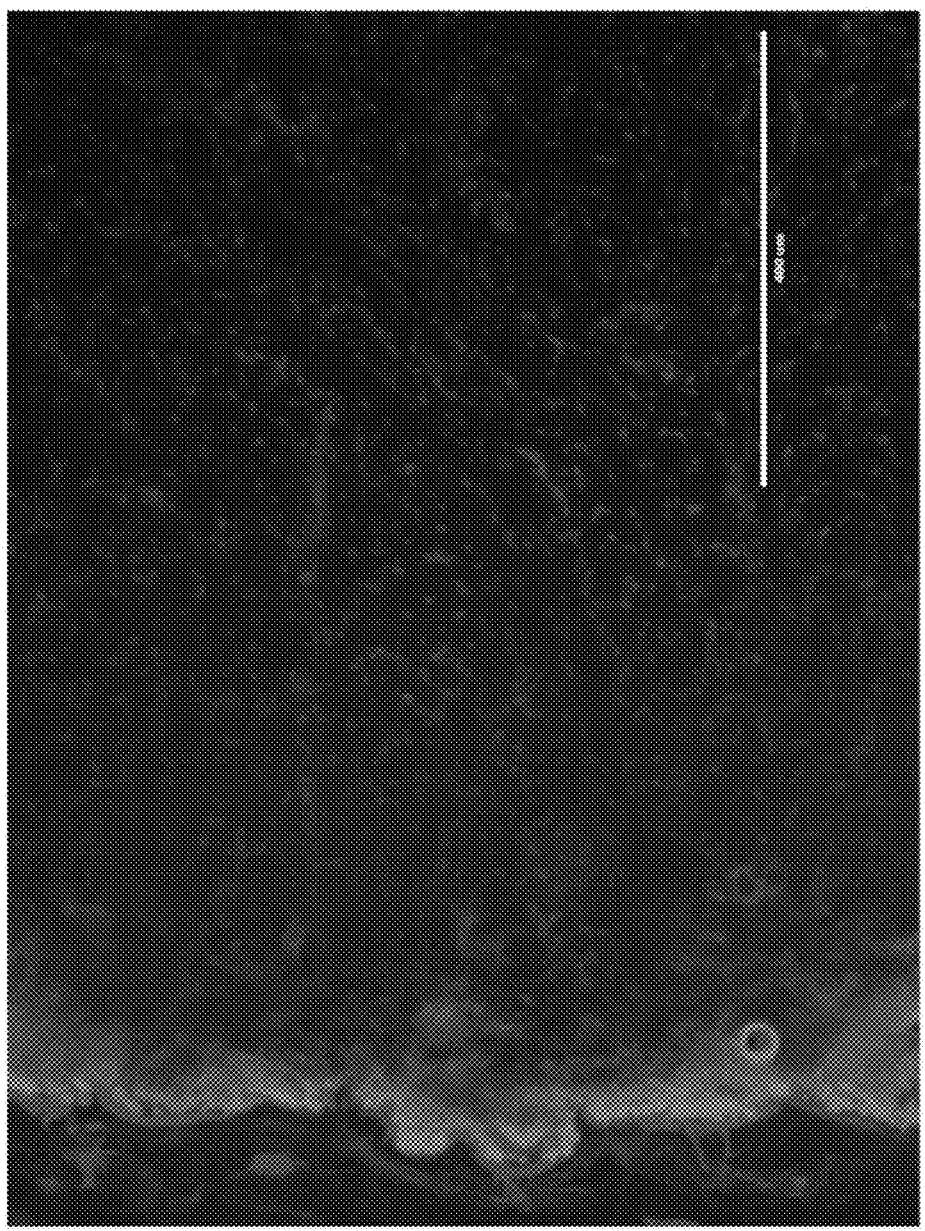
FIG. 15: Permeation of ATTO (fluorescent dye) labelled particles (red) permeating into intestinal tissue beyond the basement membrane according to embodiments of the present invention. Depth of approximately 500 μm is evident. 100× magnification.

The particles (preferably having an average diameter of 500 to 2000 nanometers (nm)) permeate the mucosal tissue of the intestine (FIGS. 14 and 15 and are taken up by intestinal stem cells (ISC's). This size is adequate to carry enough therapeutic, diagnostic or nutraceutical agent to obtain high loading and encapsulation efficiencies (higher than 80%), which is desirable for scaling up and commercialization.

The encapsulation of therapeutic, diagnostic and/or nutraceutical agents allows for controlled penetration into the mucus, by means of adding a targeting ligand, as well as a controlled release profile. Moreover, in the case of systemic penetration, the encapsulation also reduces uptake by the body's reticuloendothelial system. The smaller particles have greater surface area-to-volume ratios, which cause the particles' dissolution rates to be higher than that of larger particles.

Many agents are limited in delivery due to solubility factors. The large surface area to volume of particles increases the bioadhesivity. These factors in combination result in the penetration of the agent deep into ISCs, providing a greater benefit (FIGS. 14 and 15).

There are three main aspects of targeting that work to achieve localized delivery:

1. Charge: Positively charged polymers may used in the synthesis of the particles included in this delivery system. The resulting device exhibits a positive charge which attracts the agent-encapsulated particles to the negatively charged mucosa of the intestine.

2. Activity: Obtained using molecular targeting agents to further focus on ISCs.

3. pH: Particles in the present compositions are able to be modified to remain stable or release agents in varying pH environments, as illustrated in Example 3 under Methods of Administration. This determination takes place during the synthesis process. By synthesizing particles which keep the agent encapsulated in the highly acidic environment of the stomach and promote release in the more basic environment of the intestines, release is therefore targeted. These parameters can be changed to include release in more acidic environments or combinations thereof (FIG. 22B). These parameters can also be changed to allow for release in both the stomach and intestines. Further, varying doses and varying drug combinations are also possible. FIG. 22C shows an example of particles which release as the pH approaches neutral levels.

A. Mucoadhesive Polymeric Particles

Several bioadhesive and mucoadhesive polymers are known. In the preferred embodiment of this concept, the polymer is mucoadhesive so that it can bind to the mucosal intestinal tissue. Preferably, the polymer is polycationic, biocompatible, and biodegradable. The preferred polymer is chitosan. Chitosan is a polycationic, non-toxic, biocompatible and biodegradable polymer. Chitosan is commonly used as a mucosal agent delivery mechanism because of its bio-adhesiveness and permeability properties. The barrier in GI epithelium can easily be disrupted by chitosan particles, enhancing permeability through the mucosa.

Different factors affect fabrication of chitosan particles, such as pH of the preparation, inclusion of polyanions, charge ratios, the degree of deacetylation and the molecular weight of chitosan.

Chitosan particles have, to date, been preferred for use with chemotherapeutics for cancer treatment because of the chitosan's sensitivity to low pH. Since cancer tissue is acidic, chitosan particles release the agent faster in an acidic environment. However, in contrast to traditional uses of chitosan particles, provided herein is a novel chitosan particle synthesis process to allow for stability in acidic environments and agent release when exposed to basic conditions. The controlled release of the agent from the chitosan particles ensures that a steady amount of agent penetrates the proper GI mucosal tissue while minimizing loss and exposure to fluids and other tissue.

B. Agents to be Encapsulated

Any therapeutic, prophylactic, diagnostic or nutraceutical agent which is capable of encapsulation and release within the GI tract may be used. Representative agents include biologics, peptides, nucleotides, anti-infectives, antibiotics, antifungals, antivirals, anti-inflammatories, immunomodulators, vaccines, and combinations thereof. Preferred agents include calcium mobilizers such as nicotinic acid adenine dinucleotide phosphate and peptides such as glucagon-like peptide-2. Nicotinic acid adenine dinucleotide phosphate and other calcium mobilizers have been shown to promote ISC proliferation and intestinal epithelium regeneration. Glucagon-like peptide-2 and its analogs have also been shown to promote ISC proliferation and intestinal epithelium regeneration. The efficacy of nicotinic acid adenine dinucleotide phosphate and glucagon-like peptide-2 have been shown to be hindered by a lack of proper targeting and delivery within the GI tract. The particle-based system provided herein remedies such drawbacks.

C. Additional Additives

Other compounds which may be added include permeation enhancers and antioxidants that are useful to prevent bacterial contamination. These agents may be coated onto, encapsulated within or mixed among the agent-encapsulating particles.

Methods of Manufacture

There are at least four methods available to make chitosan particles: ionotropic gelation, microemulsion, emulsification solvent diffusion and polyelectrolyte complex. The most widely developed methods are ionotropic gelation and self-assembling polyelectrolytes. These methods offer many advantages such as simple and mild preparation conditions without the use of organic solvents or high shear forces. They are applicable to broad categories of agents including macromolecules which are notorious as labile agents. It has been found that the factors found to affect particle formation, such particle size and surface charge, also include the molecular weight and degree of deacetylation of the chitosan. The entrapment efficiency has been found to be dependent on the pKa and solubility of entrapped agents.

The ionotropic gelation method is commonly used to prepare chitosan particles. In an acidic solution, the amine group of chitosan molecules is protonized and interacts with an anion such as sodium tripolyphosphate (STPP) by ionic interaction to form particles (Lee, et al., Polymer, 42:1879-1892 (2001)). This method is very simple and mild. Reversible physical crosslinking by electrostatic interaction, instead of chemical crosslinking, may be applied to prevent possible toxicity of reagents and other undesirable effects (Shu, et al., Internal. J Pharm., 201:5158(2000)).

To improve the loading efficiency (LE), a 0/W/0 (oil/water/oil) double emulsion method was combined with temperature-programmed solidification technique and controlled PTX within the matrix network as in situ nanocrystallite form. Furthermore, these CMC particles were PEGylated, which could reduce recognition by the reticuloendothelial system (RES) and prolong the circulation time in blood. Methods of making chitosan particles by microemulsion are also known. For example, an amphiphilic graft copolymer using chitosan as a hydrophilic main chain and poly(lactic-co-glycolic acid) (PLGA) as a hydrophobic side chain is prepared through an emulsion self-assembly synthesis. A chitosan aqueous solution is used as a water phase and PLGA in chloroform serves as an oil phase. A water-in-oil (W/O) emulsion is fabricated in the presence of the surfactant span-80. TIle CS-g-PLGA amphiphile can self-assemble to form micelles with size in the range of 100-300 nm, which makes it easy to apply in various targeted-drug-release and biomaterial fields. Chitosan can be dissolved into deionized water together with 1-hydroxybenzotriazole. A water-in-oil (W/O) chitosan and poly(lactic-co-glycolic acid) microemulsion is prepared and then a chitosan-graft-poly(lactic-co-glycolic acid) stimuli-responsive amphiphile is fabricated. The obtained amphiphile can self-assemble to form micelles. In suitable solvents. Cai, Int J Nanomedicine, 6:3499-508 (2011), describes RGD peptide-mediated chitosan-based polymeric micelles targeting delivery for integrin-overexpressing tumor cells.

The cationic amino groups on the C2 position of the repeating glucopyranose units of chitosan can interact electrostatically with the anionic groups (usually carboxylic acid groups) of other polyions to form polyelectrolyte complexes. Many different polyanions from natural origin (e.g. pectin, alginate, carrageenan, xanthan gum, carboxymethyl cellulose, chondroitin sulphate, dextran sulphate, hyaluronic acid) or synthetic origin (e.g., poly (acrylic acid)), polyphosphoric acid, poly (L-lactide) have been used to form polyelectrolyte complexes with chitosan in order to provide the required physicochemical properties for the design of specific drug delivery systems (Berger et al. Eurl Pharm Biopharm. 2004; 57:35-52).

III. Methods of Administration

The particles encapsulating one or more agents may be administered via enema, capsule, solid, liquid or combination, either orally, via nasogastric tube or feeding tube, or rectally via endoscopic instruments such as an endoscope.

Example 1: Preparation of Programmable Chitosan Particles

Chitosan particles ("Particles") at varying pHs were prepared using USP grade chitosan, as described below. The particles were then subjected to incremental pH adjustments using sodium hydroxide or hydrochloric acid. The size at synthesis after each adjustment was recorded.

Impact of pH Increase

Chitosan (95% degree of deacetylation, 50 k MW) (CHI) was dissolved in 0.175% acetic acid to a final concentration of 0.2% (w/v). Sodium tripolyphosphate (STPP) was dissolved in deionized water to a final concentration of 0.2% (w/v). Particles were synthesized via the ionic gelation technique, which involves the methodical addition of an electrostatic cross-linker (TPP) to an aqueous polymer solution (CHI). The pH of the CHI solutions were adjusted with 0.1 M sodium hydroxide (NaOH) or 0.1 M hydrochloric acid (HCl) accordingly (1.0, 2.0, 2.25, 2.50, 2.75, 3.0, 4.0, 5.0 and 6.0).

Briefly, 40.0 mL of each CHI solution was added to a beaker under magnetic stirring. To this, 10.0 mL of TPP solution was added drop-wise at a constant flow rate. The Particles were allowed to stabilize for 1 hour and initial size measurements were taken using a Zetasizer Nano (Malvern Instrument Ltd., UK). The pH of the Particles was increased using 0.1 M NaOH at increments of 0.5 or 1.0 depending on the initial pH. At each step, the size and polydispersity index (PDI) were recorded.

Impact of pH Range Fluctuations

Chitosan (95% degree of deacetylation, 50 k MW) (CHI) was dissolved in 0.175% acetic acid to a final concentration of 0.2% (w/v). Sodium tripolyphosphate (STPP) was dissolved in deionized water to a final concentration of 0.2% (w/v). Particles were synthesized via the ionic gelation technique, which involves the methodical addition of an electrostatic cross-linker (TPP) to an aqueous polymer solution (CHI). The pH of the CHI solutions were adjusted with 0.1 M sodium hydroxide (NaOH) or 0.1 M hydrochloric acid (HCl) accordingly (1.0, 2.0, 3.0, 4.0, and 5.0).

Briefly, 40.0 mL of each CHI solution was added to a beaker under magnetic stirring. To this, 10.0 mL of STPP solution was added drop-wise at a constant flow rate. The Particles were allowed to stabilize for 1 hour and initial size measurements were taken using a Zetasizer Nano (Malvern Instrument Ltd., UK). The pH of the Particles were increased/decreased using 0.1 M NaOH or 0.1 M HCl at increments of 1.0 on a scale of 1.0-7.0, depending on the initial pH. The purpose of this study was to simulate the rapid and drastic pH changes of the GI tract if Particles were given orally to a patient. At each step, the size and polydispersity index (PDI) were recorded.

Impact of Polymer State

Chitosan chloride (95% degree of deacetylation, 50 k MW) (CHI) was dissolved in 0.175% acetic acid to a final concentration of 0.2% (w/v). Sodium tripolyphosphate (STPP) was dissolved in deionized water to a final concentration of 0.2% (w/v). Particles were synthesized via the ionic gelation technique, which involves the methodical addition of an electrostatic cross-linker (STPP) to an aqueous polymer solution (CHI). The pH of the CHI solutions were adjusted with 0.1 M sodium hydroxide (NaOH) or 0.1 M hydrochloric acid (HCl) accordingly (1.0, 2.0, 3.0, 4.0, & 5.0).

Briefly, 40.0 mL of each CHI solution was added to a beaker under magnetic stirring. To this, 10.0 mL of STPP solution was added drop-wise at a constant flow rate. The Particles were allowed to stabilize for 1 hour and initial size measurements were taken using a Zetasizer Nano (Malvern Instrument Ltd., UK). The pH of the Particles were increased/decreased using 0.1 M NaOH or 0.1 M HCl at increments of 1.0 on a scale of 1.0-7.0 depending on the initial pH. The purpose of this study was to simulate the rapid and drastic pH changes of the GI tract if Particles were given orally to a patient. At each step, the size and polydispersity index (PDI) were recorded. This study served to show the sensitivity of pH changes of chitosan vs. its salt derivative.

Effect of Molecular Weight & Degree of Deacetylation

Chitosan (95% degree of deacetylation, 50 k MW) (CHI) was dissolved in 0.175% acetic acid to a final concentration of 0.2% (w/v). Sodium tripolyphosphate (STPP) was dissolved in deionized water to a final concentration of 0.2% (w/v). To the chitosan, 200 µL of 60 mM sodium nitrite solution was added and the mixture stirred for 15 minutes. Without being bound to any particular theory, it is believed that this served to lower the molecular weight and the degree of deacetylation of chitosan by chemically breaking the 1,4 glycosidic bonds of the polymer. Particles were synthesized via the ionic gelation technique, which involves the methodical addition of an electrostatic cross-linker (STPP) to an aqueous polymer solution (CHI).

Briefly, 40.0 mL of each CHI solution was added to a beaker under magnetic stirring. To this, 10.0 mL of STPP solution was added drop-wise at a constant flow rate. The Particles were allowed to stabilize for 1 hour and initial size measurements were taken using a Zetasizer Nano (Malvern Instrument Ltd., UK). The pH of the Particles were increased/decreased using 0.1 M NaOH or 0.1 M HCl at increments of 1.0 on a scale of 1.0-7.0, depending on the initial pH. The purpose of this study was to simulate the rapid and drastic pH changes of the GI tract if Particles were given orally to a patient. At each step, the size and polydispersity index (PDI) were recorded. Results of this and other studies are shown in FIGS. 23, 24 and 25.

Results:

FIGS. 23, 24, and 25 summarize results of conducted studies including the properties of the particles prepared from low molecular weight chitosan. By far, the most important physical property of particulate samples is particle size. Measurement of particle size distributions is routinely carried out across a wide range of industries and is often a critical parameter in the manufacture of many products. Preferably, the particles have an average diameter of from about 500 nm to about 2000 nm.

As described in Heurtault, et al., Biomaterials, 24:4283-4300 (2003), Zeta potential is an important and useful indicator of particle surface charge, which can be used to predict and control the stability of colloidal suspensions or emulsions. Almost all particles in contact with a liquid acquire an electric charge on their surface. The electric potential at the shear plane is called the zeta potential. The shear plane is an imaginary surface separating the thin layer of liquid (liquid layer constituted of counter-ions) bound to the solid surface in motion. The greater the zeta potential the more likely the suspension is to be stable because the charged particles repel one another and thus overcome the natural tendency to aggregate. The measurement of the Zeta potential allows predictions to be made about the storage stability of a colloidal dispersion.

The charge of the particles is important for their mucoadhesiveness property (Biol Phann Bull. 2003 May; 26(5): 743-6. Positively charged materials have better mucoadhesion strength likely due to the negative charge of mucosa. Therefore, the required positive charge is within a range of 10-50 mV, which is regarded as stable.

In a separate experiment, particle were also prepared as described above, using pharmaceutical grade chitosan: PROTASAN™ UP CL 113, a commercially available formulation of chitosan chloride (FMC Corporation, Pennsylvania). PROTASAN™ UP CL 113 is based on a chitosan where between 75-90 percent of the acetyl groups are removed. The cationic polymer is a highly purified and well-characterized water-soluble chloride salt. The functional properties are described by the molecular weight and the degree of deacetylation. Typically, the molecular weight for PROTASAN™ UP CL 113 (chitosan chloride) is in the 50,000-150,000 g/mol range (measured as a chitosan acetate). The ultra-low levels of endotoxins and proteins allow for a wide variety of in vitro and in vivo applications.

Figure 23A:
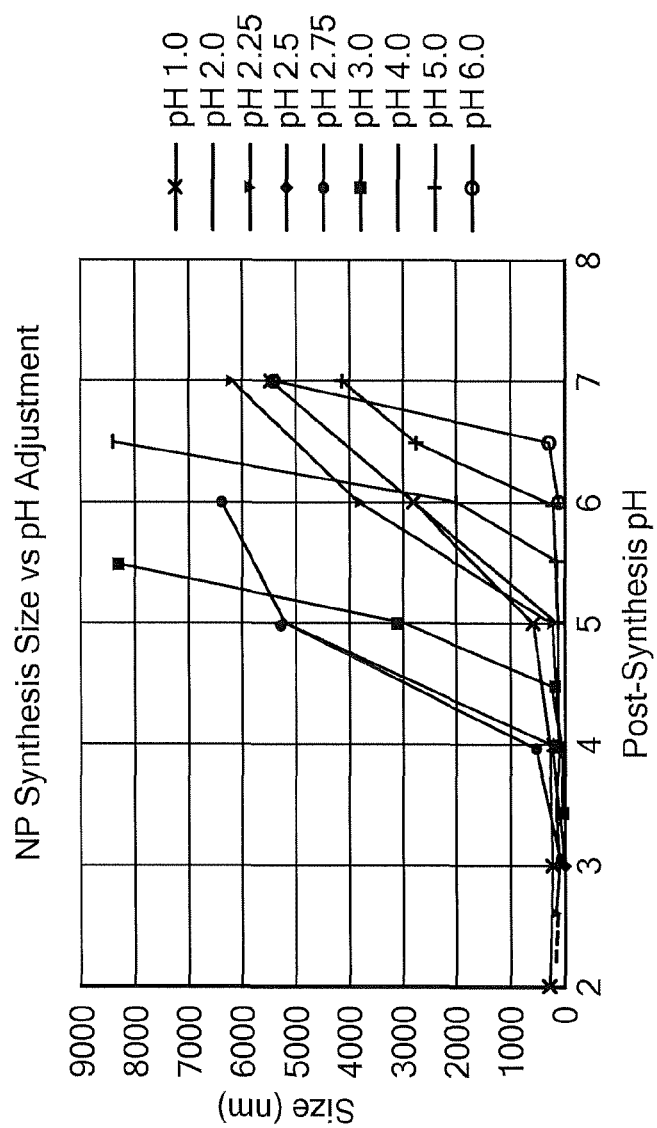
FIG. 23A: synthesis pH size vs. pH adjustment; the particles ("NPs") synthesized at pHs ranging from 1.0-6.0 showed a consistent trend in the pH of their disintegration. Nearly all of the NPs began to swell and degrade once the increased pH was a factor of 2 or more than their synthesis pH.
Figure 23B:
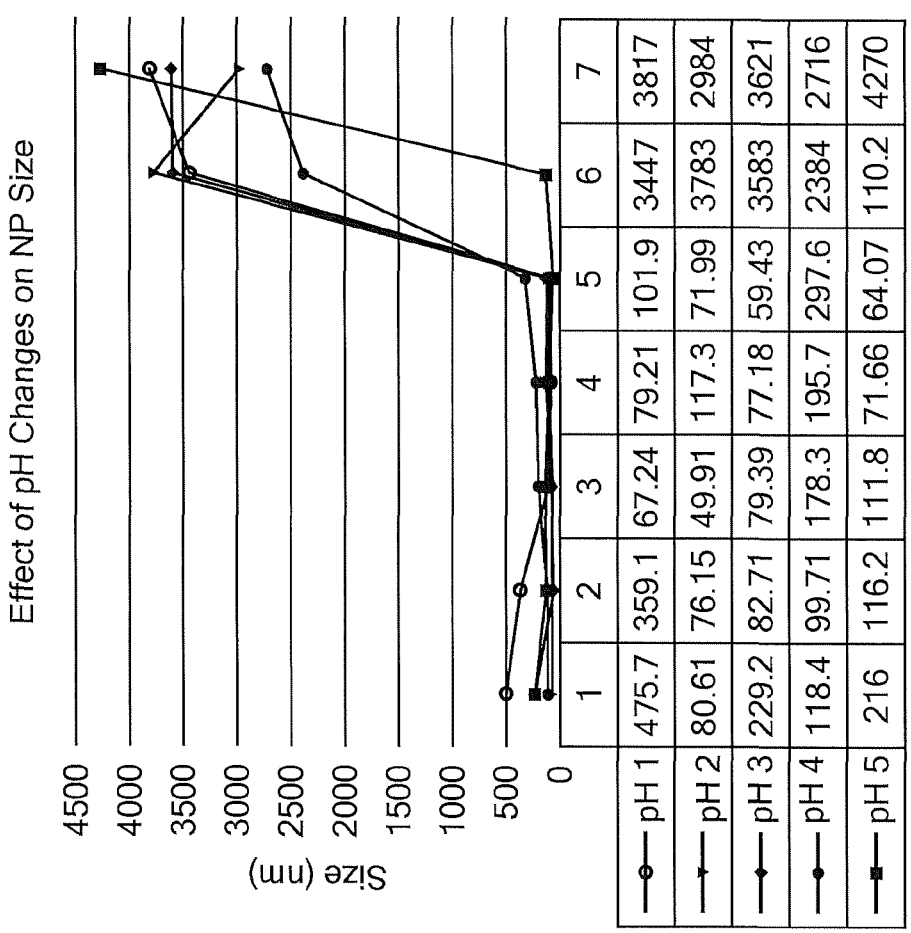
FIG. 23B: pH change to size; results show that even if NPs are synthesized at a pH of 5, for example, they can remain stable in a very acidic environment where they will not release their encapsulated drug. NPs are considered to begin releasing their payload once their size increases 400% from that of initial synthesis.
Figure 24B:
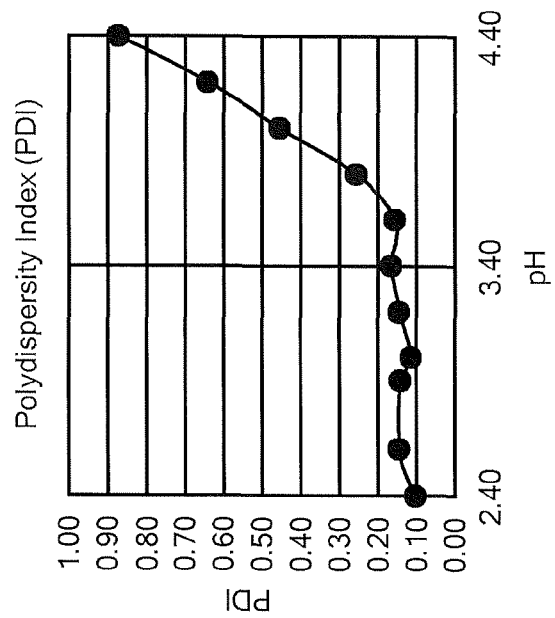
FIGS. 24A-24D: Graphs illustrating the sensitivity of one selected loaded particle ("LP") variant (FIGS. 24A and 24B) as well as graphs illustrating the level of modulation and control that can be held over particle properties (FIGS. 24C and 24D) according to embodiments of the present invention.
Figure 24A:
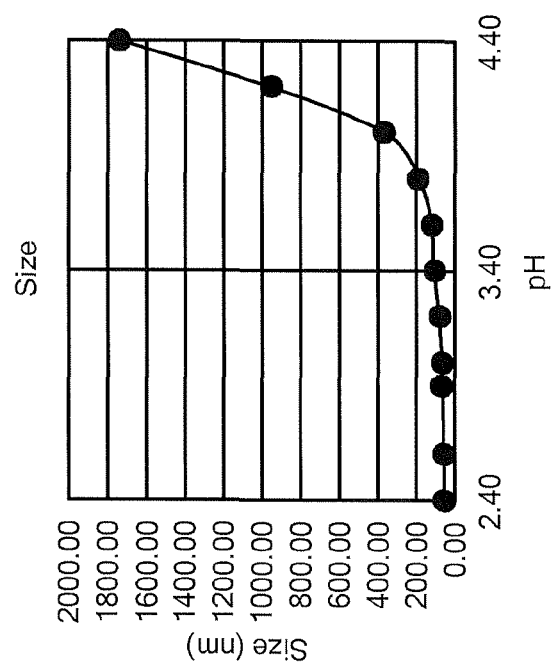
Figures 24C, 24D:
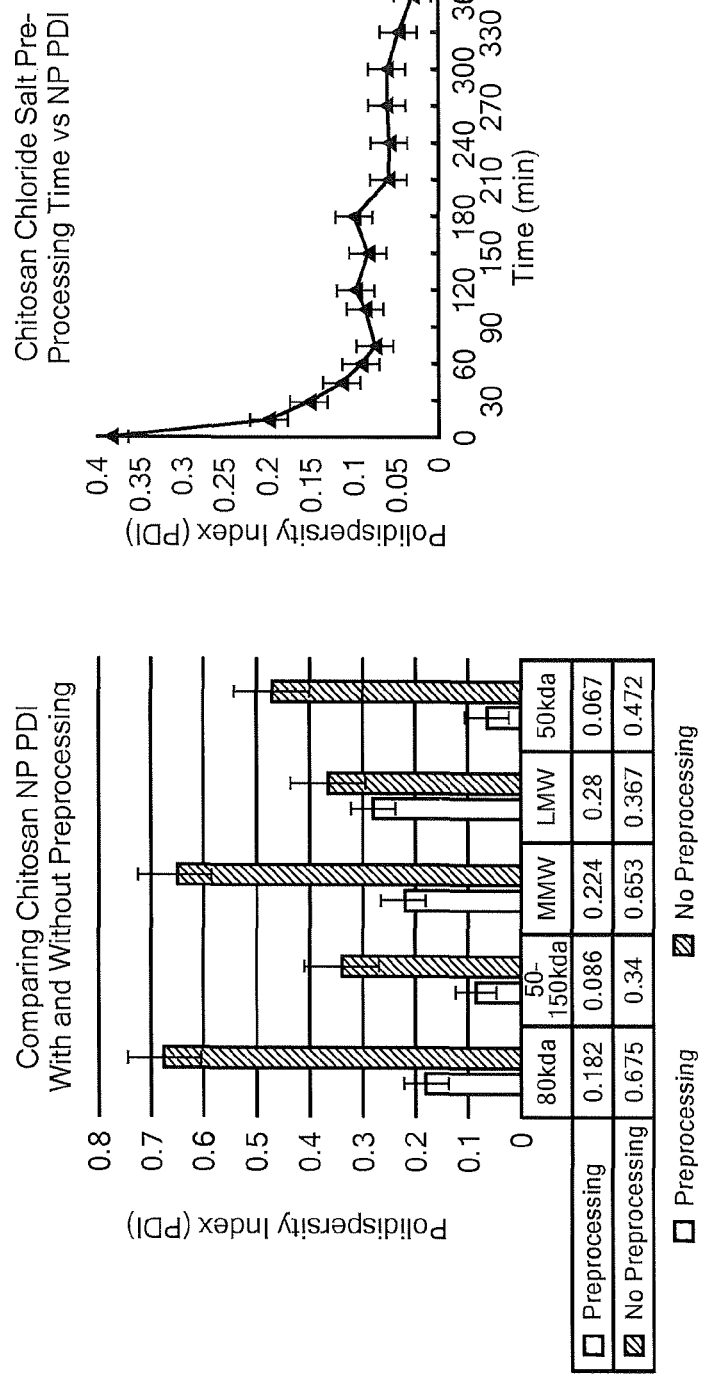
Figures 25A, 25B:
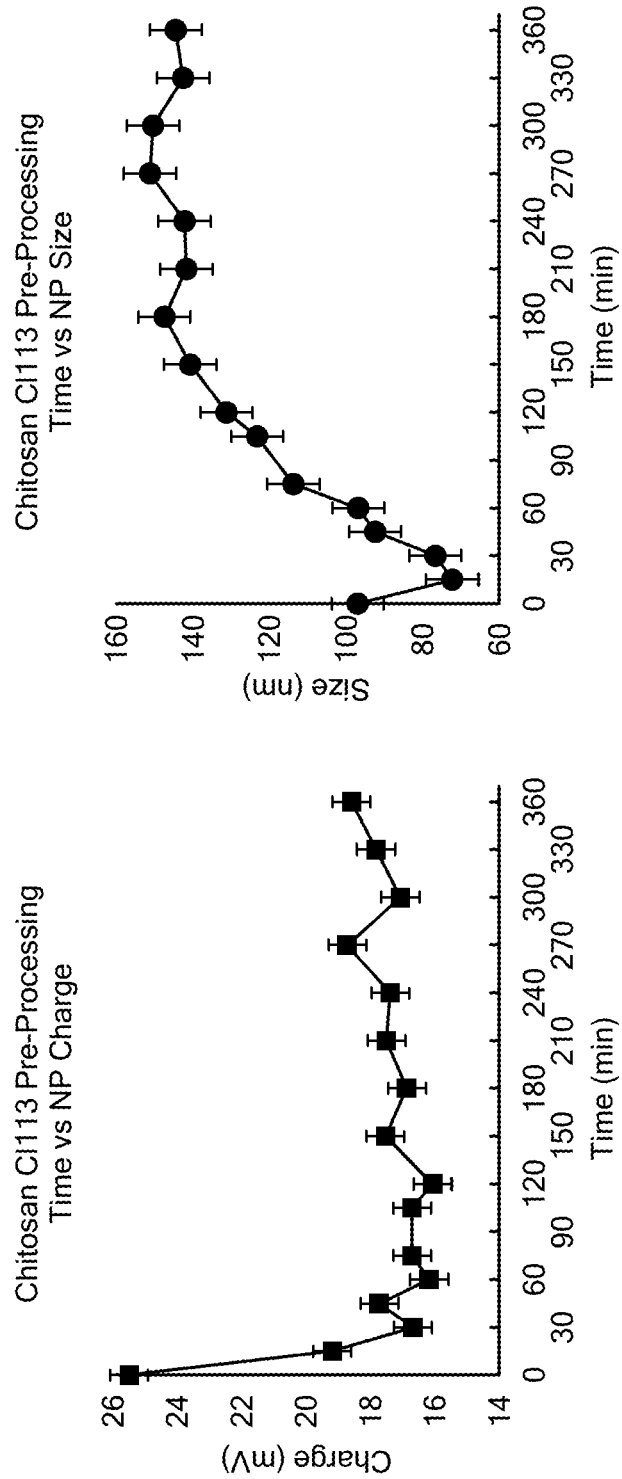
FIGS. 25A-25D: Charts demonstrating an example of how the charge (FIG. 25A) and size (FIGS. 25B, 25C, and 25D) of chitosan loaded particles can be precisely modulated.
Figures 25C, 25D:
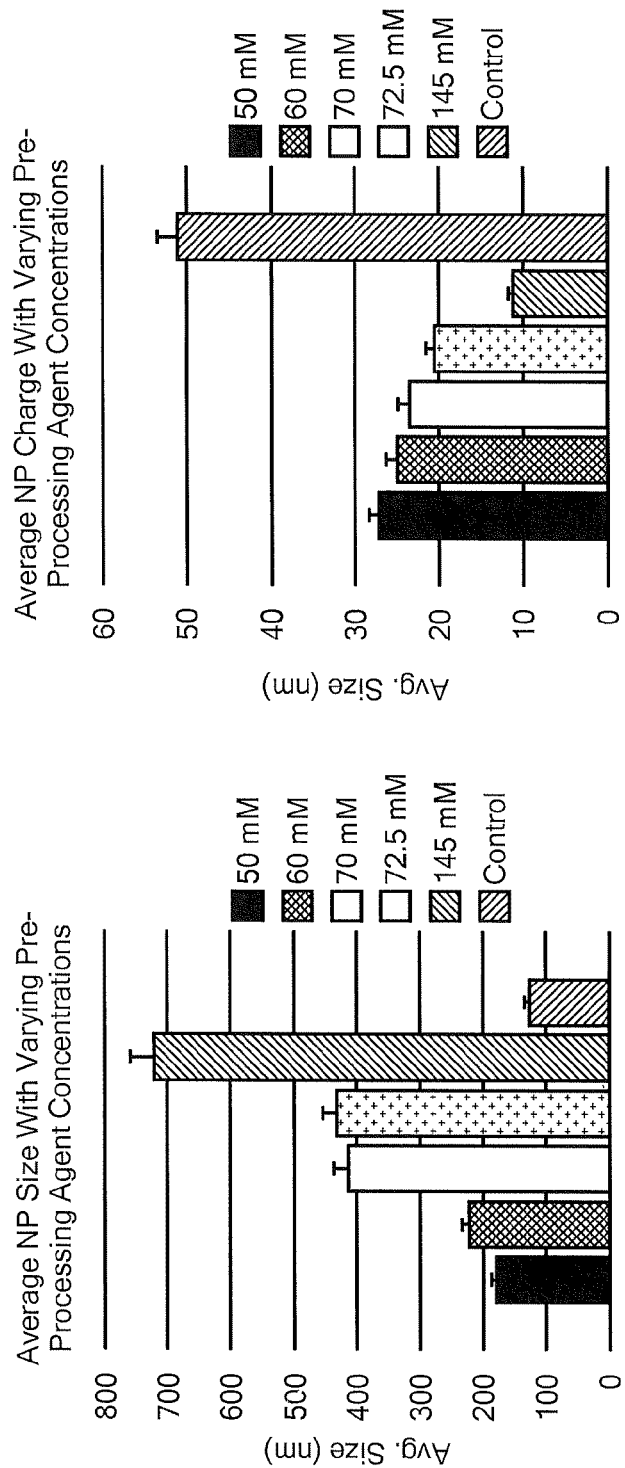

The graphs of FIG. 23A-23C show the properties of certain particles in different situations, including FIG. 23A: synthesis pH size vs pH adjustment; FIG. 23B: pH change to size; FIG. 23C: pH change to polydispersity index (PDI). The graphs of FIGS. 24A-24D illustrate the sensitivity of one selected loaded particle ("LP") variant (FIGS. 24A and 24B) as well as the level of modulation and control that can be held over particle properties (FIGS. 24C and 24D). The charts of FIGS. 25A-25D demonstrate an example of how the size (FIGS. 25A and 25D) and charge (FIGS. 25B and 25C) of chitosan loaded particles can be modulated using different concentrations of preprocessing agents such as sodium nitrite.

By using high purity chitosan (the cationic polymer was a highly purified and well-characterized water-soluble chloride salt), chitosan particle of better quality were obtained. The optimal formulation was obtained by optimizing different ratios between the STPP and chitosan solution (0.6:1; 0.5:1; 0.4:1). The best formation was achieved with a ratio of STPP to chitosan of about 0.5:1, which had the ideal size and zeta potential.

Example 2

Effect of pH on the size, zeta potential and stability of chitosan particle. This technology is advantageous because of its ability to be customized to remain stable in desired pH environments and release in other desired pH environments. This is accomplished in part by modulating the pH during the particle synthesis process. An example of the effect of the synthesis pH on the release of particle is summarized in FIG. 26, with the effect on size and Polydispersity Index (PDI) shown.

As shown in FIGS. 26A-26E, the polydispersity index (PDI) and size of the particle change depending on the pH environment introduced after synthesis, as seen by comparing the results obtained at pH 3.4 (FIG. 26A), pH 1 (FIG. 26B), pH 2 (FIG. 26C) pH. For this example, a PDI of approximately 0.40 or lower is preferable. Since the polymer making up the particles used above expands to release the encapsulated drug, a larger size indicates that the particles have degraded and released.

Figure 27:
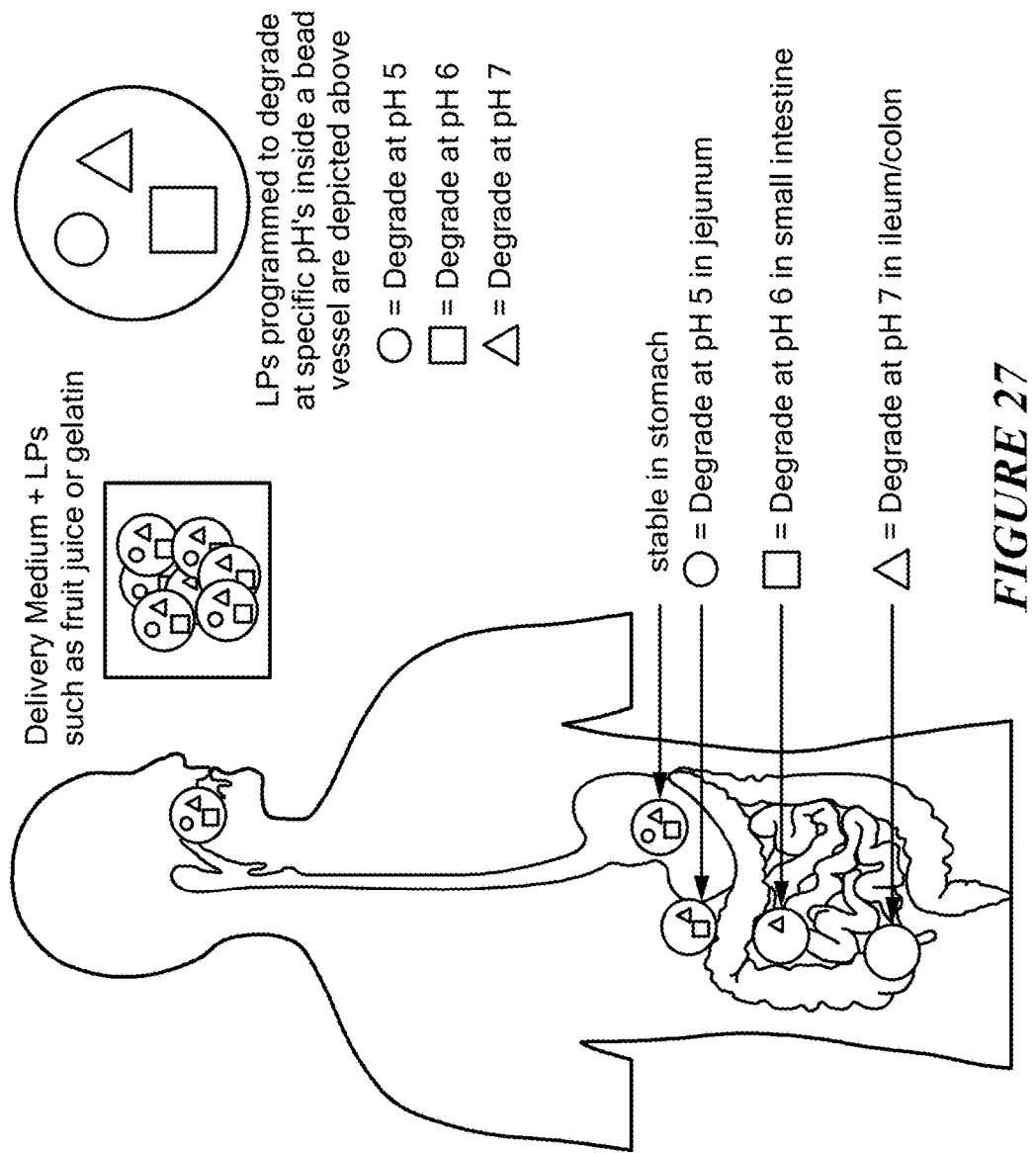
FIG. 27: Illustration demonstrating how particles can be created to release at specific desired regions within the GI tract according to embodiments of the present invention.

As shown in FIG. 27, the pH of the human intestines range dramatically, and drug delivery systems which are able to be customized to control release according to pH are highly effective at targeting. For example, according to the example data shown above, Particles synthesized at pH 1 are able to remain stable from pH range 3-5 and release in a lower or higher environment. A patient that is administered these particles alongside some other supplement would experience targeted release within the ileum. Likewise, other formulations can yield particles that can promote delivery all across the GI tract.

Figure 20:
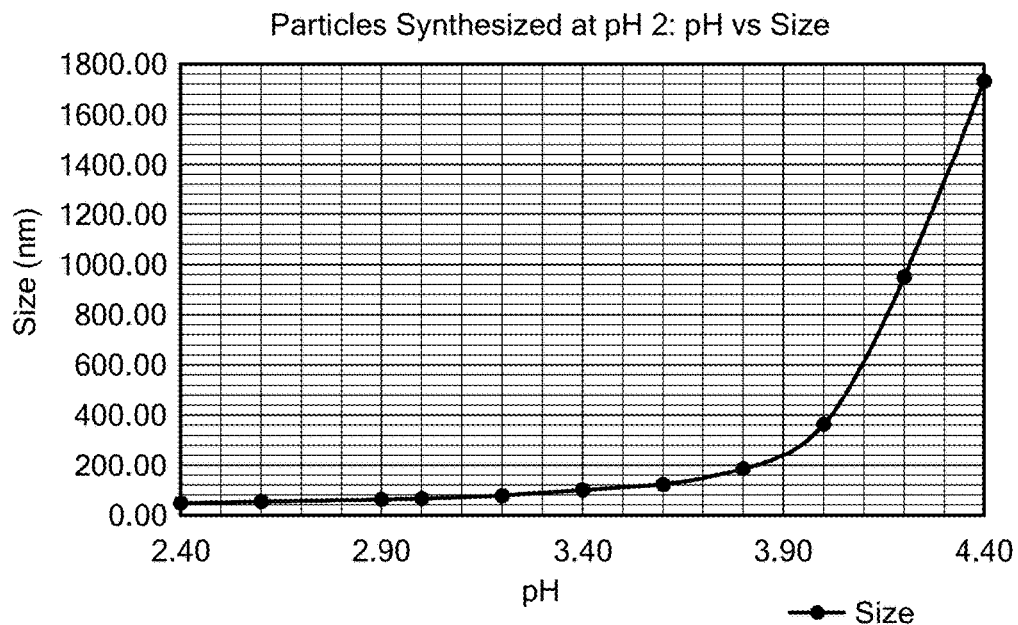
FIG. 20: Image showing an example of the relationship of pH to size of particles in some embodiments of the present invention.
Figure 21:
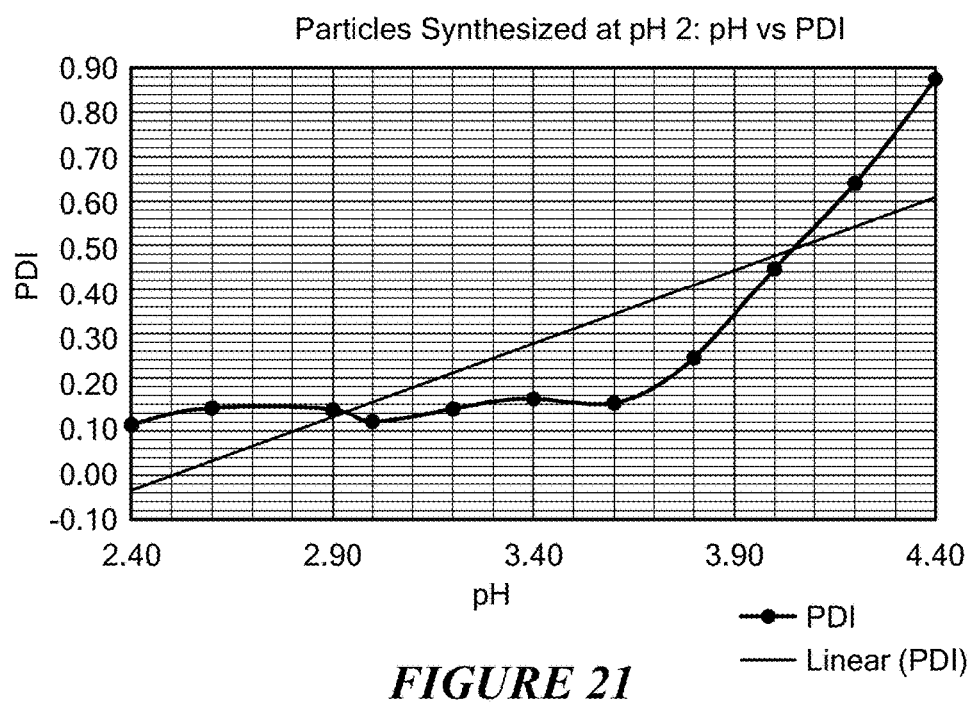
FIG. 21: Image showing an example of the relationship of pH to PDI (defined below) of particles in some embodiments of the present invention.

In another embodiment, particles have been designed to remain stable at pH levels of 2-4 and release at environments above pH 4. FIG. 20 and FIG. 21 illustrate this. FIG. 20 plots the dependency of the size of particles (as measured by a Malvern Zetasizer Nano) on the pH. The size is seen increasing sharply at levels at and above pH 4. When the particles release the encapsulated agent, they swell in size, so this increase indicates that the agent has been released. Likewise, FIG. 21 plots the pH to PDI of the particles.

In another embodiment, particles with different stability and release properties are combined in one delivery method to facilitate delivery to more than one location within the GI tract despite differences in pH. FIG. 27 illustrates the design of this system.

As shown in FIG. 27, the inclusion of particles with different properties in the delivery medium allow for delivery of particles and subsequent degradation within various regions of the GI tract. This is advantageous over traditional methods of agent delivery due to its enhanced targeted ability and non-reliance on merely one "stable" pH range and where the particles release encapsulated agent.

Example 4: Optimization of NP at Large Scale

Automation of processes is especially necessary in nanotechnology applications where the product properties are very sensitive to changes.

Materials and Methods for Automated Particle Synthesis:

All the reagents and chemicals used are excipient or pharmaceutical grade

Solution A: 0.1% (active agent) in 0.1% Tripolyphosphate (STPP) solution

Solution B: 0.1% Chitosan (CL 113) in 0.175% acetic acid solution

Place 10 mL solution B in a glass beaker and stir at 600 rpm on magnetic stirrer. Transfer a total of 10 mL Solution A drop wise on the stirred solution B with the help of a peristaltic pump or any other pump that can provide a constant flow rate, as used herein at 1.5 mL/min, but which may be modified to yield a different size, charge, polydispersity, NP yield, and drug encapsulation efficiency properties.

Different ratios of solutions A to solution B (A:B) were used from 1:1 (as in the above case) to 1.1:0.85. Different mixing ratios produce different NP properties. Gradually increase the stirring speed of solution B to 650 rpm at the time when half of the solution A has been transferred. When transfer of solution A is completed, gradually increase the stirring speed to 700 rpm and then gradually add disaccharide trehalose to the solution to obtain a final trehalose concentration of 2%. Continue stirring until all the added trehalose has been dissolved (or for at least 10 min) to equilibrate the solution. Measure the Z-average, the polydispersity index (PDI), the mean diameter of each peak, and NP yield (count rate) of the obtained Particles. The following storage steps are followed.

For storage, the final NP solution is placed in a proper container and is frozen using liquid nitrogen, in dry ice, or in ultra-low temperature freezer until complete freezing obtained and then they are freeze-dried until complete elimination of solvent is obtained.

NP Solution

Scalability is essential for mass production. Drug carrying particles are formed in a solution environment by self-assembly, which is a dynamic process that takes place only under the correct chemical conditions. This technique is extremely sensitive to manufacturing variables including mixing rate of subsequent solutions and their concentrations, freshness, and purity. The mixing rate of subsequent solutions cannot be increased above a certain value without sacrificing particle properties. Furthermore, due to the dynamic nature of self-assembly, the mixing process must be finished in a limited time as any delays in this duration increases the chance of deviation of particle properties or yield from optimal values. The sensitive nature of self-assembly production methodologies enforces adoption of strictly controlled batch type manufacturing processes and does not allow high production volumes per batch. An automated system has been developed which has successfully adapted the original manual particle production processes into an automated version and can now strictly control the properties of the resulting particle including size, polydispersity, and encapsulation efficiency. These parameters are of prime importance in terms of efficacy of the drug delivery system as well as raw material costs. Parameters can be adjusted to obtain a balance between maximal batch volume and particle yield (number of particles formed in a particular production batch) while keeping the properties of particles within narrow tolerances. Polydispersity of the obtained particles was found to be well within acceptable ranges.

Targeted Delivery of Agents for the Treatment of Colorectal and Anal Diseases

In a further aspect, a drug delivery device has been developed to administer agents in a highly targeted manner within the colonic, rectum, and/or anal tissue. This device is in the form of a mesh, or mesh-like material, and is topically applied onto the anus, perianal area or through the anal canal onto affected tissue in need of agent delivery. The mesh releases agents encapsulated within microparticles for controlled and targeted treatment of diseases. The mesh is able to deliver microparticles through the mucosa or other tissue with which it comes in contact, to deliver a concentrated dosage of agents locally, in a more targeted manner than traditional systemic delivery of agents. This allows for greater safety and efficacy of agents within the body. The microparticles included within the mesh provide retention of the agent or agents locally and/or regionally within the tissue to which the mesh was applied. If desired, free agents within the mesh but not within the particles may also be included, for example to achieve agent delivery from the local tissue into systemic circulation of the body.

The mesh formulation utilizes microparticles to target drug delivery and alter release parameters which can treat or prevent diseases, or otherwise deliver agents to the colon, rectum, or anal tissue to treat, prevent and/or diagnose diseases. The use of microparticles allows passage through the mucosa lining the tissue of the colon, rectum, and/or anus, ensuring a sufficient and targeted agent delivery.

The formulation of this mesh includes agent-encapsulating microparticles. The properties of these microparticles are able to be changed to modulate the release depending on the region of the gastrointestinal tract being treated. For example, microscopically, the rectum is lined by high columnar mucus-producing cells. The anal canal is divided into three zones with different type of epithelium lining; the proximal zone is lined by stratified cuboidal epithelium, while the intermediate (pectin zone) is lined by stratified squamous epithelium but without adnexae (e.g., hair, sebaceous glands). And the distal (the anal skin) is lined by squamous stratified epithelium and contains hair and sebaceous glands. To this end, different sizes of particles may be required in order to permeate and release the encapsulated agent within the specific affected region, maximizing the specificity of the delivery. The size and charge of the particles may be customized to provide for the adequate treatment of each region. This further allows for the development of an optimal personal treatment customized for the location and disease.

The microparticles are formed of a polymer such as chitosan, and will include at least one agent to be delivered. This delivery system may optionally include permeation enhancers, either included within the mesh or externally administered to the targeted tissue prior to, during, or after mesh administration. Any permeation enhancer or permeation enhancers administered will affect at least the tissue of the colon, rectum, and/or anus. They may be administered via enema, liquid, suppository, orally administered capsule, tablet, injection, within the mesh itself or via other delivery means.

Figure 28:
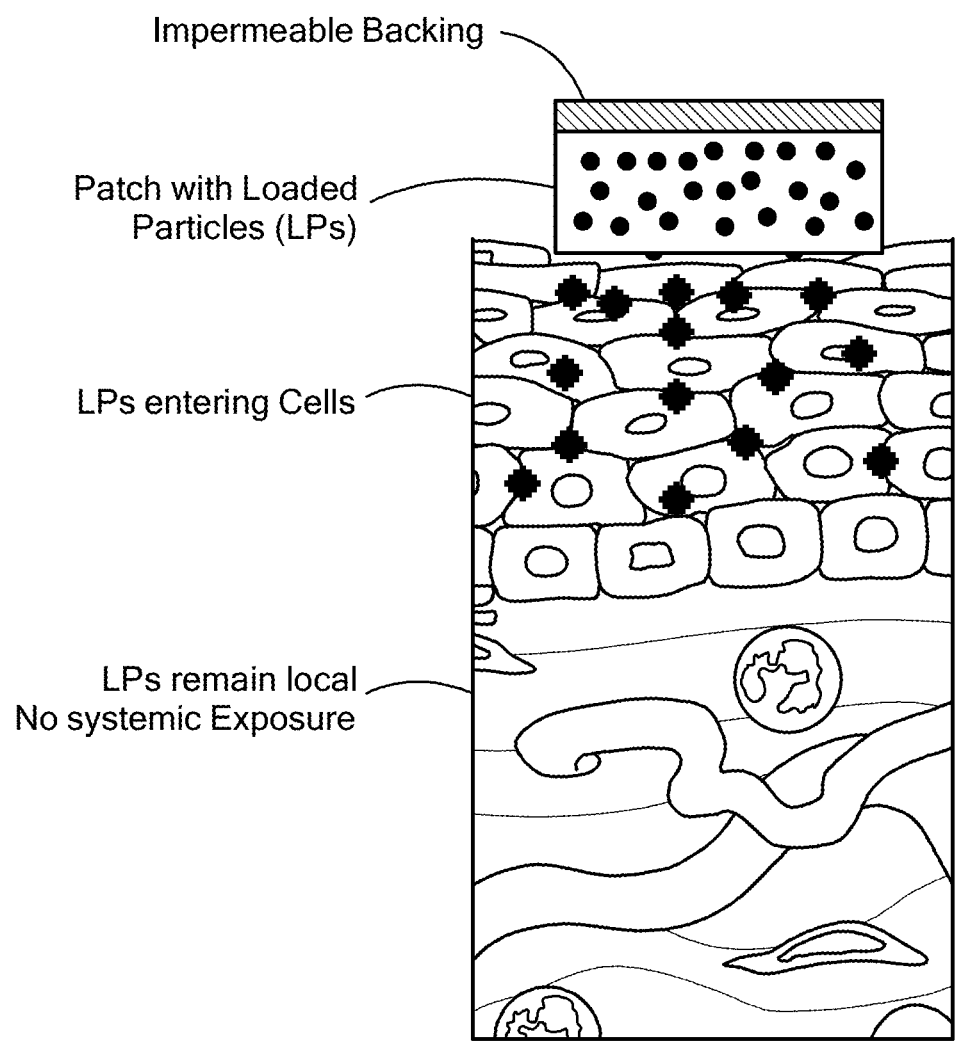
FIG. 28 illustrates a mesh containing microparticles for unidirectional delivery through either the mucosa or epithelium lining the colon, rectum or anal tissue as outlined in the description delivering microparticles into the tissue, according to embodiments of the present invention. The mesh depicted contains an optionally impermeable or water permeable backing layer to prevent passage of materials through the reverse side of the mesh, and illustrates how loaded particles released permeate the tissue locally.

In the preferred embodiment, the mesh is formed with one side exposed for contact with the appropriate tissue. As illustrated in FIG. 28, particles containing the agent or agents will be released from this side upon contact with the appropriate tissue. Also in the preferred embodiment, the other side facing the external gastrointestinal cavity may be covered with a backing film, layer, or other impermeable membrane to prevent loss of the agent from the mesh into the gastrointestinal system, or contamination of the mesh via fluids or other matter in the gastrointestinal system. Optionally, the impermeable film, layer, or membrane may be replaced with a water-permeable film, layer, or membrane.

The mesh described herein can also be included as one component of a larger treatment kit intended for the treatment of colon, rectal and/or anal diseases. This kit may include materials that are required for proper administration of the mesh as well as proper and safe disposal of the mesh after application and cleaning of the treated area. For example, 5-fluorouracil, mitomycin and cisplatin are commonly used chemotherapeutics for the treatment of anal cancer. And either the FOLFOX (5-FU, leucovorin, and oxaliplatin) or CapeOx (capecitabine and oxaliplatin) regimens are used most often in treating colorectal cancer. These chemotherapeutics are highly potent and toxic, however, and extensive precautions must be taken to ensure that proper handling procedures are followed during treatment, and contact is minimized between these agents and both the patient and personnel applying the mesh. Items that may then be included in the kit for the purpose of safety, such as a cleansing enema to be administered before and/or after application of the mesh, forceps or other tools for the placement of the mesh, disposable packaging for any remaining portion of the mesh after application, and any other instruments which may be required to safely administer the mesh.

A topical agent delivery mesh has been developed specifically for delivery of agents within the rectal, colonic, and/or anal tissue. Preferably, the mesh is at least partially made of biodegradable and/or biocompatible materials. The microparticles released from the mesh are preferably locally or regionally retained within the colonic, rectal, and/or anal tissue under and around which the mesh was applied. The majority of the one or more agents released from the microparticles is preferably locally or regionally retained within the colonic, rectal, and/or anal tissue under and around which the mesh was applied.

Figure 29:
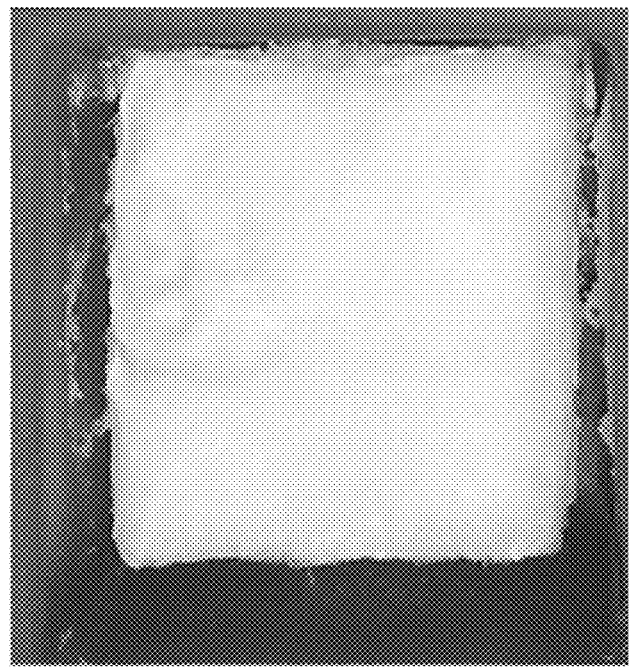
FIG. 29 is an image of one style of the mesh according to embodiments of the present invention within a protective mold.
Figure 32:
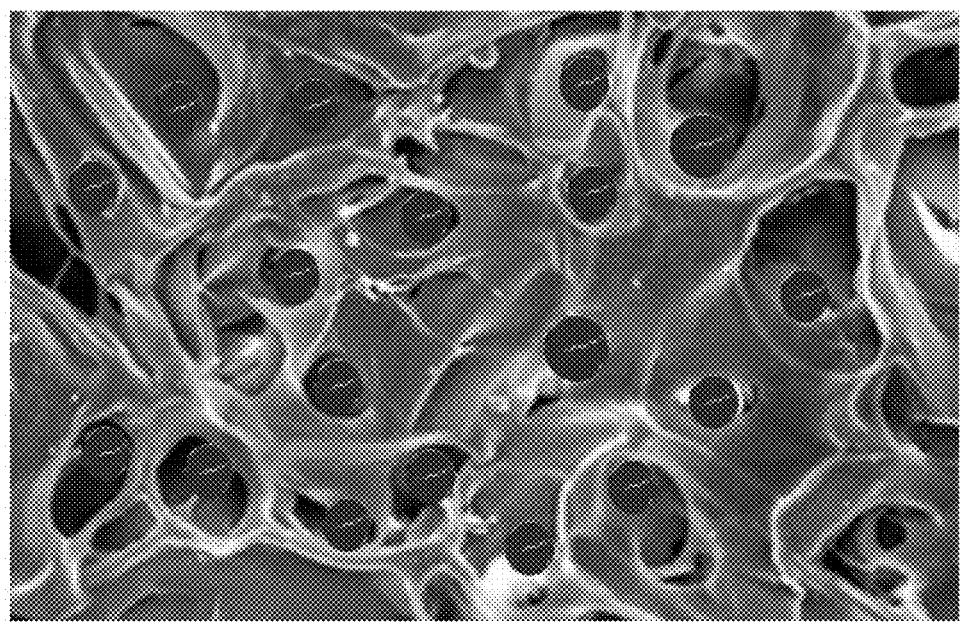
FIG. 32 shows the mesh containing particles inside of it according to embodiments of the present invention.

The Mesh:

The mesh includes microparticles and an optional backing layer for delivery through mucosa, epithelium, or both, and delivers microparticles into neighboring tissue (FIG. 28). The mesh can take multiple forms, typically synthesized within a mold to control its shape (FIG. 29). Microparticles can be seen within the mesh (FIG. 32) and help to form its structure. It can be seen that microparticles offer significant contribution to the mesh structure. The microparticles include a polymer, and optionally targeting elements (FIG. 13). The mesh is applied to the tissue of the gastrointestinal tract via the anus, preferably onto a mucus layer but also onto epithelium of the anus where no mucus is present, allowing delivery of the agent to the underlying cells. The microparticles penetrate the mucosa/epithelium and release the agent or agents directly into the tissue. The mesh may be formed of bioadhesive polymer.

In the preferred embodiment, chitosan is used as the polymer for the microparticles. Chitosan is a deacetylated derivative of chitin, the second most abundant polysaccharide, and has a large density of reactive groups and a wide range of molecular weights. Chitosan is considered useful as a bioadhesive material because of its ability to form non-covalent bonds with biological tissues, mainly epithelia and mucous membranes. Bioadhesions formed using natural polymers have unique properties as a carrier because they can prolong residence time and, therefore, increase the absorbance of loaded drugs. Chitosan is a bioabsorbable, biocompatible, biodegradable, anti-bacterial and non-toxic polymer.

In addition, chitosan has different functional groups that can be modified. Because of its unique physicochemical properties, chitosan has great potential in a range of biomedical applications. Chitosan can be used as a delivery mechanism because of its bio-adhesiveness as well as its established ability to act as an absorption and permeation enhancer. The barrier in mucosa or epithelium can easily be disrupted by chitosan particles, enhancing permeability through mucosa.

Figure 31:
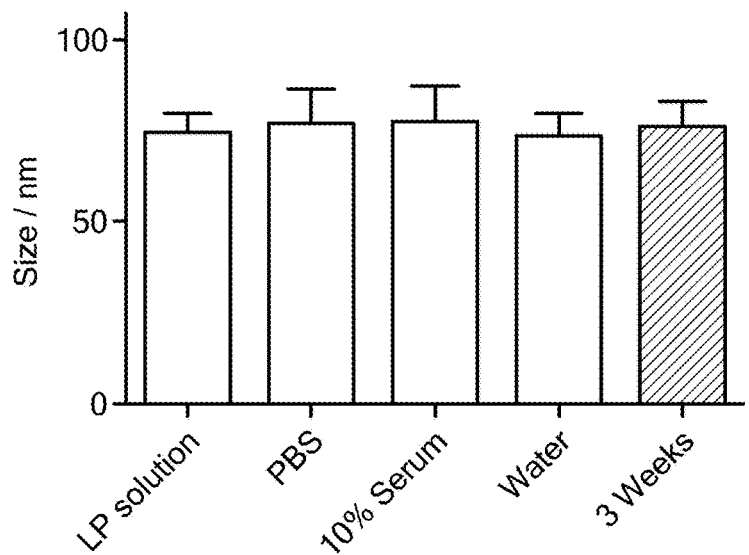
FIG. 31 shows a graph detailing the stability of particles in various solutions.

The most widely developed particle manufacturing methods are ionotropic gelation and self-assembling polyelectrolytes. These methods offer many advantages such as simple and mild preparation method without the use of organic solvent or high shear force. They are applicable to broad categories of agents including macromolecules which are notorious as labile agents. Usually, the factors found to affect particles formation, including particle size and surface charge, are molecular weight and degree of deacetylation of chitosan. The particles may be tailored to be stable in a variety of environments (FIG. 31).

The ionotropic gelation method is commonly used to prepare chitosan particles. This method is based on electrostatic interaction; at physiologic pH, the primary amine groups of chitosan are protonated, and therefore chitosan is positive-charged. The positive charge is used to form particles in solution via cross-linking with polyanions (stabilizer) such as sodium tripolyphosphate (STPP), to efficiently encapsulate the drug via electrostatic interaction, and to promote cellular internalization of drug-containing chitosan particles. Several advantages of this simple and mild method include the use of aqueous solutions, the preparation of particles with a small size, the manipulation of particle size by the variation in pH values, and the possibility of encapsulation of drug during particle formation. Structural changes can be introduced by ionic strength variations like presence of KCl at low and moderate concentrations emphasize swelling and weakness of chitosan-STPP ionic interactions, in turn particle disintegration.

Figure 30:
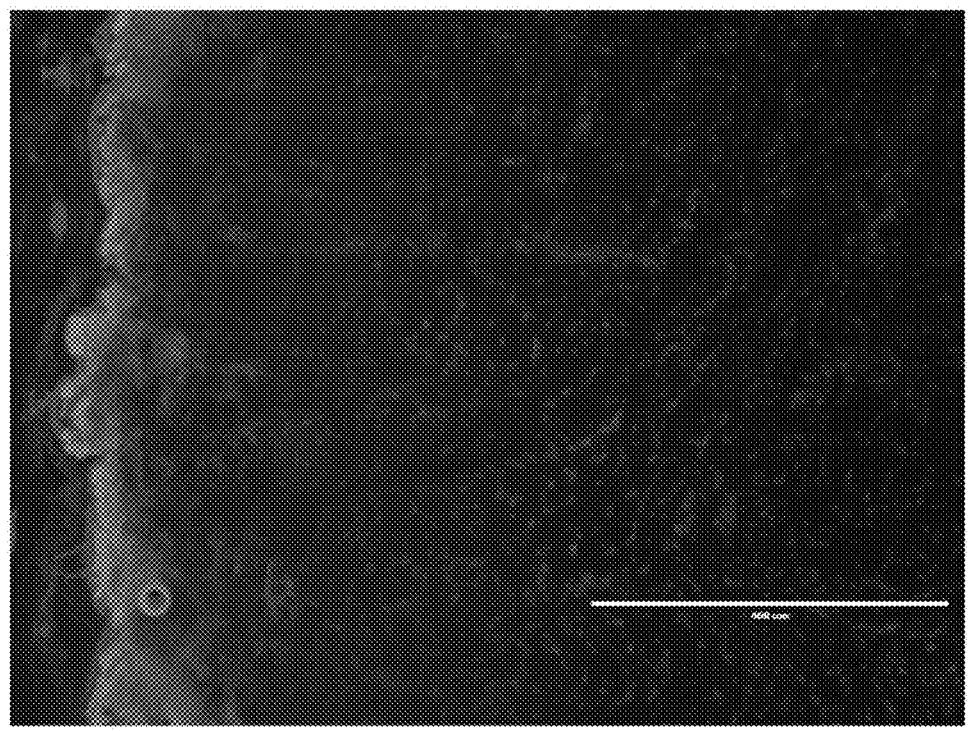
FIG. 30 is an image showing the fluorescent permeation of one style of the mesh within tissue. The mesh was administered and left in contact with the tissue for one hour. particles have been conjugated to ATTO (fluorescent dye) which fluoresces red as shown in the image. The blue color is DAPI staining which stains the nuclei of cells blue. The scale bar shown is 400 μm, showing that the red particles have permeated significantly into the blue tissue.
Figure 33:
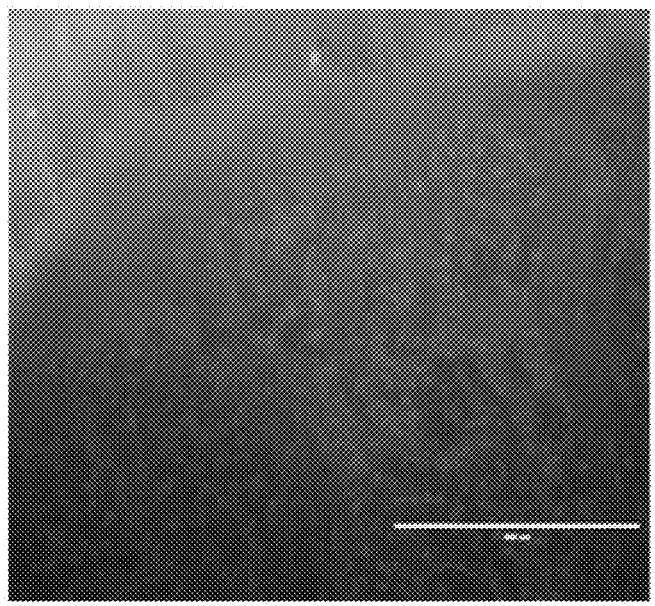
FIG. 33 shows the level of permeation by one embodiment of the present invention. The green fluorescence represents particles which have permeated the tissue.

The particles (micro- but also nano-sized particles) can permeate the tissue within the anus, colon, or rectum. The size is dependent on the pH of the solution and the weight ratio of Chitosan to STPP. And the size of the particles influences the drug release rates. Permeation is important to the efficacy of the mesh, and the mesh has been shown to have very high permeation ability (FIGS. 30 and 33). This size is adequate to carry enough of the included agent or agents such as a chemotherapeutic to obtain high loading and encapsulation efficiencies. The encapsulation also protects the outer tissue in the GI tract from damage if toxic agents such as chemotherapeutics are included. Other parameters affect the particles including the chitosan: stabilizer (such as STPP) ratio in aqueous solution during the synthesis process, as an increase in the amount of stabilizer leads to a higher degree of chitosan cross-linking and a decrease in the particle dimensions.

The embodiments of the described above are intended to be merely exemplary; numerous variations and modifications will be apparent to those skilled in the art. All such variations and modifications are intended to be within the scope of the present invention as defined in any appended claims.

REFERENCES

"Burns: Types, Treatments, and More." Healthline. N.p., n.d. Web. 28 Jun. 2016. www.healthline.com/health/burns#Overview1.
"What Is Melanoma Skin Cancer?" What Is Melanoma Skin Cancer? N.p., n.d. Web. 28 Jun. 2016. www.cancer.org/cancer/skincancer-melanoma/detailedguide/melanoma-skin-cancer-what-is-melanoma.
"The Oral Cancer Foundation." The Oral Cancer Foundation. Oral Cancer Foundation, n.d. Web. 27 Jun. 2016.
"First Aid: Burns." First Aid: Burns. N.p., n.d. Web. 28 Jun. 2016. familydoctor.org/familydoctor/en/prevention-wellness/staying-healthy/first-aid/first-aid-burns.html.
"Psoriasis Foundation." Psoriasis Foundation, n.d. Web. 28 Jun. 2016. www.psoriasis.org%2Fabout-psoriasis.
"Causes and Triggers." Psoriasis Causes and Known Triggers. N.p., n.d. Web. 29 Jun. 2016. www.psoriasis.org/about-psoriasis/causes.
"Skin Cancer Foundation." Melanoma. N.p., n.d. Web. 29 Jun. 2016. www.skincancer.org/skin-cancer-information/melanoma.
"Mucositis." Mucositis. Oral Cancer Foundation, n.d. Web. 21 Jan. 2016.
Weinberg M A, Estefan D J. "Assessing oral malignancies". AmFam Physician. 2002, 65 (7): 1379-1384
"The Oral Cancer Foundation." The Oral Cancer Foundation. Oral Cancer Foundation, n.d. Web. 21 Jan. 2016.
"Mucositis." Mucositis. Oral Cancer Foundation, n.d. Web. 21 Jan. 2016.
Gillenwater A, Papadimitrakopoulou, V, Richards-Kortum, R. "Oral Premalignancy: New Methods of Detection and Treatment". Curr Oncol Rep. 2006 March; 8(2): 146-154
Jacobson J J, Epstein J B, Eichmiller F C, Gibson T B, Carls G S, Vogtmann E, Wang S, Murphy B. "The cost burden of oral, oral pharyngeal, and salivary gland cancers in three groups: commercial insurance, Medicare, and Medicaid." Head and Neck Oncology 2012; 4:15. doi: 10.1186/1758-3284-4-15. Epub 2012 Apr. 26.
jco.ascopubs.org/content/26/29/4731.full
Barker, N. van de Wetering, M. Clevers H. "The intestinal stem cell". Genes & Dev 2008 22:1856-1864
Shaw, D. Gohil, K. Basson M. "Intestinal mucosal atrophy and adaptation" 2012 18(44): 6357-6375
www.medscape.com/viewarticle/820753
Hookman, Perry, and Jamie S. Barkin. "*Clostridium difficile* associated infection, diarrhea and colitis." World journal of gastroenterology: WJG 15.13 (2009): 1554.
www.chp.edu/~/media/chp/departments-and-services/pediatric-surgery/documents/enema-administration.ashx?la=en
Youssef N N, Barksdale E J, Griffiths J M, Flores A F, Di Lorenzo C. "Management of Intractable Constipation With Antegrade Enemas in Neurologically Intact Children" Journal of Pediatric Gastroenterology & Nutrition. 2002 34(4): 402-405
Hanauer, S B, Robinson M, Pruitt R, Lazenby A J, Persson T, Nilsson G, Walton-Bowen K, Haskell L P, Levine J G. "Budesonide enema for the treatment of active, distal ulcerative colitis and proctitis: A dose-ranging study". Gastroenterology 115(3) 1998 525-532.
patient.info/doctor/prescribing-for-children
Murata Y, Sasaki N, Miyamoto E, Kawashima S. "Use of floating alginate gel beads for stomach-specific drug delivery". Eur J Pharm Biopharm. 2000 September; 50(2):221-6
Laksitorini M, Prasasty V D, Kiptoo P K, Siahaan T J. "Pathways and progress in improving drug delivery through the intestinal mucosa and blood-brain barriers." Ther Deliv. 2014 5(10):1143-63. doi: 10.4155/tde.14.67.
Lai, S. Wang, Y. Hanes J. "Mucus-penetrating nanoparticles for drug and gene delivery to mucosal tissues". Adv Drug Deliv Rev. 2009 Feb. 27; 61(2): 158-171
Bhandari, Bhesh. "Food Materials Science and Engineering" 2012 section 8.2: Nutrient Digestion and Absorption in the Gastrointestinal Tract
www.livestrong.com/article/312184-the-three-phases-of-the-food-digestion-process/
Living with Anal Cancer—Causes & Risk Factors—the HPV and Anal cancer foundation website.
Cancer of the Anus, Anal Canal, and Anorectum—fact sheet, Surveillance, Epidemiology, and End Result program (SEER), NIH.
Cancer of the Colon and Rectum—fact sheet, Surveillance, Epidemiology, and End Result program (SEER), NIH.
fightcolorectalcancer.org/fight-it/managing-side-effects/
Anatomy and Histology of the Small and Large Intestine-jpck.zju.edu.cn/jcyxjp/files/ge/05/MT/0511.pdf
Clinical features, staging, and treatment of anal cancer—uptodate.com.
Clinical presentation, diagnosis, and staging of colorectal cancer—uptodate.com
Colorectal Cancer—Detailed guide, American Cancer Society. Cancer.org.
Glynne-Jones, R., et al. "Anal cancer: ESMO Clinical Practice Guidelines for diagnosis, treatment and follow-up." Annals of Oncology 21.suppl 5 (2010): v87-v92.
Living with Anal Cancer/Treatment for Anal Cancer, the HPV and Anal cancer foundation—website.
Paun, Bogdan C., et al. "Postoperative complications following surgery for rectal cancer." Annals of surgery 251.5 (2010): 807-818.
Koh P K, Tang C L, Eu K W, et al. A systematic review of the function and complications of colonic pouches. Int J Colorectal Dis. 2007; 22:543-548.
Adjuvant therapy for resected rectal adenocarcinoma—uptodate.com.
Gupta K C, Kumar R. Drug release behavior of beads and microgranules of chitosan. Biomaterials 2000; 21: 1115-1119.
Kulkarnia A R, Soppimatha K S, Aminabhavia T M, Rudzinskib W E. In-vitro release kinetics of cefadroxil-loaded sodium alginate interpenetrating network beads. European Journal of Pharmaceutics and Biopharmaceutics 2001; 51: 127-133.

Liu, Z. et al., Adv. Drug Deliv. Rev. 2008, 60, 1650-1662.

Bardot, P. M.; et al. Presses universitaires de Franche-Comte' mars 2009. 308, ISBN: 2-84867-249-8.

Patil, Poonam, Daksha Chavanke, and Milind Wagh. "A review on ionotropic gelation method: novel approach for controlled gastroretentive gelispheres." Int J Pharm Pharm Sci 4.4 (2012): 27-32.

Zhang, Zheng, et al. "Polymeric nanoparticles-based topical delivery systems for the treatment of dermatological diseases." Wiley Interdisciplinary Reviews: Nanomedicine and Nanobiotechnology 5.3 (2013): 205-218.

Zhang, Hong, et al. "Monodisperse chitosan nanoparticles for mucosal drug delivery." Biomacromolecules 5.6 (2004): 2461-2468.

[21] Nagpal, Kalpana, Shailendra Kumar Singh, and Dina Nath Mishra. "Chitosan nanoparticles: a promising system in novel drug delivery." Chemical and Pharmaceutical Bulletin 58.11 (2010): 1423-1430.

What is claimed is:

1. A system for delivery of a therapeutic agent to a site in mucosal tissue, the system comprising:
    a porous, mucoadhesive, freeze-dried polymeric matrix, having first and second opposed surfaces, the matrix formed by a composition including:
        chitosan,
        a hydration promoter,
        a microparticle adhesion inhibitor, comprising HPMC, and
        a microparticle aggregation inhibitor in a concentration of 0.1% to 50% by weight, and
    a plurality of microparticles, having an average diameter between 500 nm and 2000 nm, embedded within the matrix so as to be directly surrounded by, and in contact with, the matrix, the microparticles containing a therapeutic agent and having a coating around the therapeutic agent,
    wherein:
(i) the first surface of the matrix is configured to be attached to the site in the mucosal tissue and the matrix is configured to provide controlled release of the microparticles, through the first surface, when the first surface of the matrix is thus attached to the site;
(ii) the coating includes chitosan so as to provide controlled release of the agent from the microparticles; and
(iii) the hydration promoter, the microparticle adhesion inhibitor, and the microparticle aggregation inhibitor are compounds mutually distinct from one another and present in amounts sufficient to achieve the controlled release of the microparticles without preventing formation of the freeze-dried matrix.

2. A system according to claim 1, wherein the hydration promoter is selected from the group consisting of ethylene glycol, propylene glycol, beta-propylene glycol, glycerol and combinations thereof.

3. A system according to claim 1, wherein the microparticle aggregation inhibitor is selected from the group consisting of monosaccharides, disaccharides, sugar alcohols, chlorinated monosaccharides, chlorinated disaccharides, and combinations thereof.

4. A system according to claim 1, wherein the microparticles further include sodium tripolyphosphate.

5. A system according to claim 1, further comprising a free amount of the therapeutic agent, embedded directly in the matrix, and not otherwise coated with chitosan, wherein the free amount of the therapeutic agent constitutes between 20-80% of a total amount of the therapeutic agent in the system.

6. A system according to claim 1, wherein the second surface is permeable to water.

7. A system according to claim 6, wherein the second surface includes a material selected from the group consisting of a polyacrylate adhesive, a non-woven polyester fabric, and combinations thereof.

8. A system according to claim 1, wherein the chitosan in the matrix and the chitosan in the microparticles is pure chitosan.

9. A system according to claim 1, wherein the therapeutic agent is a chemotherapeutic pharmaceutical.

10. A system according to claim 1, wherein the chitosan of the microparticles is pure chitosan.

* * * * *